(12) United States Patent
Chen et al.

(10) Patent No.: US 8,703,804 B2
(45) Date of Patent: Apr. 22, 2014

(54) RYANODINE RECEPTOR INHIBITORS AND METHODS RELATING THERETO

(75) Inventors: S. R. Wayne Chen, Calgary (CA); Thomas G. Back, Calgary (CA); Dawei Jiang, Brookline, MA (US); Kannan Vembaiyan, Ottawa (CA)

(73) Assignee: UTI Limited Partnership, Calgary (CA)

( * ) Notice: Subject to any disclaimer, the term of this patent is extended or adjusted under 35 U.S.C. 154(b) by 910 days.

(21) Appl. No.: 11/728,834

(22) Filed: Mar. 26, 2007

(65) Prior Publication Data

US 2007/0254849 A1 Nov. 1, 2007

Related U.S. Application Data

(60) Provisional application No. 60/743,782, filed on Mar. 26, 2006.

(51) Int. Cl.

| | | |
|---|---|---|
| A01N 43/64 | (2006.01) | |
| A61K 31/41 | (2006.01) | |
| A01N 43/76 | (2006.01) | |
| A61K 31/42 | (2006.01) | |
| A01N 43/04 | (2006.01) | |
| A61K 31/70 | (2006.01) | |
| C07D 209/82 | (2006.01) | |

(52) U.S. Cl.
USPC .............. 514/359; 514/375; 514/25; 548/440

(58) Field of Classification Search
USPC .............................. 514/359, 375, 25; 548/440
See application file for complete search history.

(56) References Cited

U.S. PATENT DOCUMENTS

| 4,503,067 A | 3/1985 | Wiedemann et al. .......... 514/411 |
| 2003/0105138 A1 | 6/2003 | Lukas-Laskey et al. ...... 514/330 |

FOREIGN PATENT DOCUMENTS

| CA | 1129416 | 8/1982 |
| CA | 2392085 | 5/2001 |
| CA | 2447005 | 11/2002 |
| CA | 2462275 | 4/2003 |

OTHER PUBLICATIONS

Maier, N. M., Uray, G. (1996) Efficient high-performance liquid chormatographic enantioseparatioin of five-membered aryl-substituted lactones and cyclic carbamates on a (R,R)-diaminodihydroethanoanthracene-derived chiral stationary phase. Journal of Chromatograph A, vol. 740, p. 11-19.*
Baartscheer et al., "SR calcium handling and calcium after-transients in a rabbit model of heart failure," *Cardiovasc Res.*, 58:99-108, 2003.
Bers, "Cardiac excitation- contraction coupling," *Nature*, 415:198-205, 2002.
Bristow et al., "Carvedilol Produces Dose-Related Improvements in Left Ventricular Function and Survival in Subjects With Chronic Heart Failure," *Circulation*, 94:2807-2816, 1996.
Butler et al., "Perturbing effects of carvedilol on a model membrane system: role of lipophilicity and chemical structure," *Biophys Chem.*, 119:307-315, 2006.
Farrell et al., "beta-Blockers in heart failure: clinical applications," *JAMA*, 287:890-897, 2002.
Gheorghiade and Eichhorn, "Practical aspects of using beta-adrenergic blockade in systolic heart failure," *Am J Med.*, 110:68S-73S, 2001.
Hjalmarson, "Cardioprotection with beta-adrenoceptor blockers. Does lipophilicity matter?," *Basic Res Cardiol.*, 95:I41-5, 2000.
Jiang et al., "Enhanced store overload-induced Ca2+ release and channel sensitivity to luminal Ca2+ activation are common defects of RyR2 mutations linked to ventricular tachycardia and sudden death," *Circ. Res.*, 97:1173-1181, 2005.
Jiang et al., "RyR2 mutations linked to ventricular tachycardia and sudden death reduce the threshold for store-overload-induced Ca2+ release (SOICR)," *Proc. Nat. Acad. Sci. USA*, 101:13062-13067, 2004.
Ko et al., "Adverse effects of beta-blocker therapy for patients with heart failure: a quantitative overview of randomized trials," *Arch Intern Med.*, 164:1389-1394, 2004.
Lakatta, "Functional implications of spontaneous sarcoplasmic reticulum Ca2+ release in the heart," *Cardiovasc Res.*, 26:193-214, 1992.
Nakai et al., "Primary structure and functional expression from cDNA of the cardiac ryanodine receptor/calcium release channel," *FEBS Lett.*, 271:169-177, 1990.
Okafor et al., "Chronic treatment with carvedilol improves ventricular function and reduces myocyte apoptosis in an animal model of heart failure," *BMC Physiol.*, 3:6, 2003.
Otsu et al., "Molecular cloning of cDNA encoding the Ca2+ release channel (ryanodine receptor) of rabbit cardiac muscle sarcoplasmic reticulum," *J Biol Chem.*, 265:13472-13483, 1990.
Pogwizd and Bers, "Cellular basis of triggered arrhythmias in heart failure," *Trends in Cardiovascular Medicine*, 14:61-66, 2004.
Sanguinetti and Bennett, "Antiarrhythmic Drug Target Choices and Screening," *Circ Res.*, 93:491-499, 2003.
Schwarz et al, "Cardioprotection by Carvedilol: antiapoptosis is independent of beta-adrenoceptor blockage in the rat heart," *J Cardiovasc Pharmacol Ther.*, 8:207-215, 2003.
Vermeulen et al., "Triggered activity and automaticity in ventricular trabeculae of failing human and rabbit hearts," *Cardiovasc Res.*, 28:1547-1554, 1994.
Yao et al., "Characteristic effects of alpha1-beta1,2-adrenergic blocking agent, carvedilol, on [Ca2+]i in ventricular myocytes compared with those of timolol and atenolol," *Circ J.*, 67:83-90, 2003.
Zhao et al., "Molecular identification of the ryanodine receptor pore-forming segment," *J Biol Chem.*, 274:25971-25974, 1999.
PCT International Search Report and Written Opinion, issued in International Application No. PCT/IB2007/003006, dated Feb. 4, 2008.

* cited by examiner

*Primary Examiner* — Scarlett Goon
(74) *Attorney, Agent, or Firm* — Parker Highlander PLLC

(57) ABSTRACT

The present invention provides novel ryanodine receptor type 2 (RyR2) inhibitors and methods of their use in the treatment of cardiac conditions. In general, the RyR2 inhibitors of the present invention assist in the normalization of intracellular calcium homeostasis. In certain embodiments, the RyR2 inhibitors are store-overload-induced $Ca^{2+}$ release (SOICR) inhibitors that minimally inhibit or do not inhibit $Ca^{2+}$-induced $Ca^{2+}$ release (CICR), thereby providing beneficial effects in cardiac therapy.

20 Claims, 13 Drawing Sheets
(4 of 13 Drawing Sheet(s) Filed in Color)

Fig.1
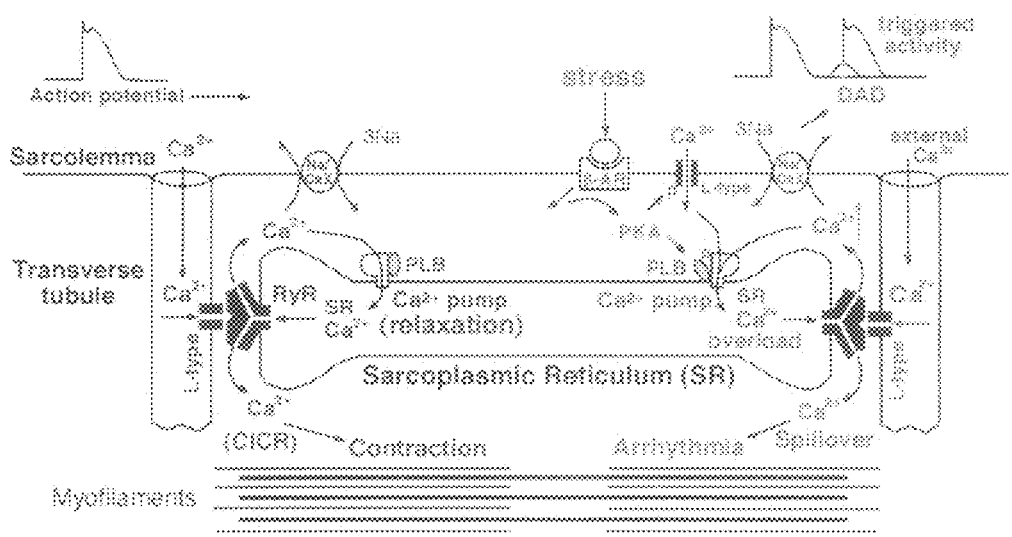
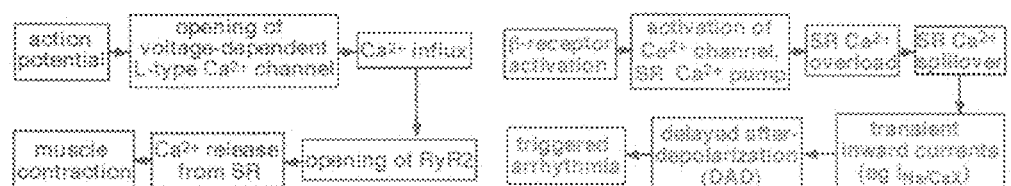

Fig. 2
A. Normal Sarcoplasmic Reticulum
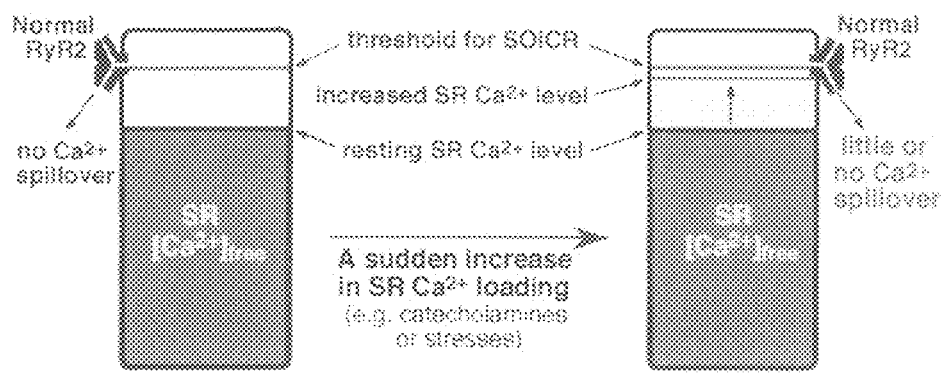
B. Abnormal Sarcoplasmic Reticulum
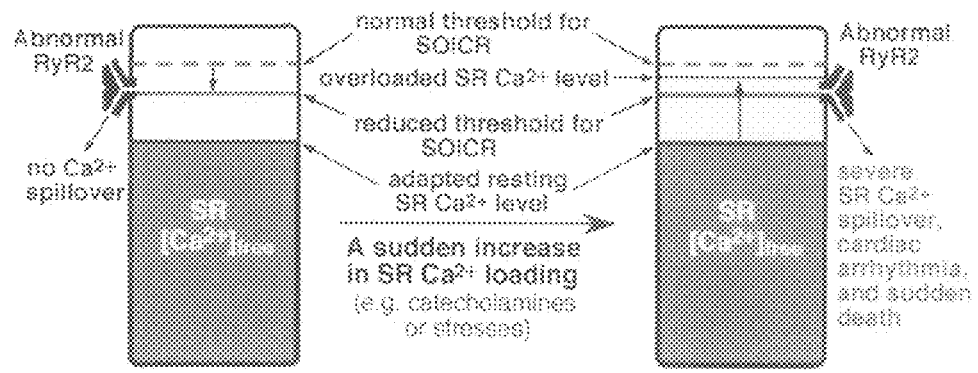

Certain Compounds of the Present Invention

Scheme 1

Scheme 3

Scheme 5

RYANODINE RECEPTOR INHIBITORS AND METHODS RELATING THERETO

This application claims the benefit of U.S. Provisional Application No. 60/743,782, filed Mar. 26, 2006, the contents of which are incorporated herein in their entirety.

BACKGROUND OF THE INVENTION

1. Field of the Invention

The present invention relates generally to the fields of cardiac muscle disorders and diseases. More particularly, the present invention relates to ryanodine receptor inhibitors and uses thereof for the treatment and prevention of conditions associated with extracellular calcium imbalance in cardiac muscle. The ryanodine receptor inhibitors of the present invention may serve as, for example, anti-arrhythmia agents. The ryanodine receptor inhibitors may also have reduced β-blocking activity.

2. Description of Related Art

Heart failure is a common, progressive and often fatal cardiac condition. Heart failure is responsible for millions of hospitalizations and over 300,000 deaths in the U.S. and over a million in Western countries annually, resulting in an enormous impact on public health. A leading cause of death in patients with heart failure is arrhythmia. The primary therapeutic strategy over the last several decades has been to suppress arrhythmias by the use of anti-arrhythmic drugs. Gheorghiade and Eichhorn, 2001. There are currently several types of drugs available on the market to treat various types of arrhythmias.

Of a number of anti-arrhythmic drugs used over the past several decades, β-blockers are the only class of anti-arrhythmic drugs proven to have significant survival benefits, and have become the most widely used drugs for the treatment of heart failure and cardiac arrhythmias. Foody et al., 2002. Although β-blockers have revolutionized the treatment of patients with these diseases, the absolute benefit of β-blocker treatment is low (~7% absolute reduction in all-cause mortality). Miller, 2003. Clearly, there is a need in the art for new anti-arrhythmic drugs with better efficacy.

SUMMARY OF THE INVENTION

The present invention provides compounds that modulate calcium regulation for cardiac therapy. In certain embodiments, compounds of the present invention modulate calcium release. In particular embodiments, these compounds are store-overload-induced $Ca^{2+}$ release (SOICR) inhibitors. For example, the present inventors have determined that certain SOICR inhibitors are ryanodine receptor type 2 (RyR2) inhibitors. These and other RyR2 inhibitors, some of which are derivatives of carvedilol, may have attenuated β-blocking activity relative to the β-blocking activity of carvedilol itself, a feature that may provide improved benefits in cardiac therapy.

Therefore, in one aspect, the invention contemplates compounds defined by formula (I):

(I)

wherein:
$R_1$ is selected from the group consisting of H, lower alkyl, upper alkyl, lower alkylsulfonate, upper alkylsulfonate, —C(O)-lower alkyl, —C(O)-upper alkyl and acyl;
$R_2$ is selected from the group consisting of cycloalkyl, —$OSO_3^-$, a sugar, and phenyl optionally mono-, di- or tri-substituted with a group selected from halogen, lower alkyl and lower alkoxy;
$R_3$ is —CH—,
$R_4$ is —$CH_2$—;
$R_3$ and $R_4$ are joined by a single or double bond;
$R_5$ and $R_6$ are each independently selected from the group consisting of H, lower alkyl and acyl, or
$R_5$ and $R_6$ together form —C(O)—, —$(CH_2)_p$—, —$(CH_2)_qC(O)$— or —$C(O)(CH_2)_r$—, wherein p=1-7 and q and r are independently 1-6; and
m, n and o are each independently 1-5;

provided that when $R_1$ is H and $R_3$ and $R_4$ are single bonded, the following provisos apply:
when $R_5$ and $R_6$ are each —$C(O)CH_3$, then $R_2$ is not 2-methoxyphenyl;
when $R_5$ is —C(O)-t-butyl and $R_6$ is H, then $R_2$ is not 2-methoxyphenyl;
when $R_5$ and $R_6$ together form —C(O)—, then $R_2$ is not 2-methoxyphenyl; and
when $R_5$ is H or $C_1$-$C_6$ acyl, $R_6$ is H or $C_1$-$C_6$ alkyl, then $R_2$ is not phenyl that is mono- or di-substituted with any combination of halogen, $C_1$-$C_6$ alkyl, or $C_1$-$C_6$ alkoxy;
and provided that when $R_1$ is H, $R_3$ and $R_4$ are single bonded, and $R_5$ is H, the following provisos apply:
when $R_6$ is —$C(O)CH_3$, then $R_2$ is not 2-methoxyphenyl;
when $R_6$ is methyl or n-butyl, then $R_2$ is not 2-methoxyphenyl; and
when $R_6$ is H, then $R_2$ is not phenyl, 2-methylphenyl, 3-methylphenyl, 2,3-dimethylphenyl, 4-t-butylphenyl, 2-methoxyphenyl, 3-methoxyphenyl, 4-methoxyphenyl, 2-ethoxyphenyl, 2-chlorophenyl, 4-fluorophenyl, 5-fluoro-2-methoxyphenyl, or 2,6-dimethoxyphenyl.

In certain embodiments, $R_1$ of the compound of formula (I) is hydrogen. In certain embodiments, $R_1$ is methyl. $R_2$ may be any aryl group, as defined herein. In certain embodiments, $R_2$ is phenyl. When $R_2$ is phenyl, the phenyl group may optionally be mono-, di- or tri-substituted with a group selected from halogen, lower alkyl and lower alkoxy. When $R_2$ is phenyl, the phenyl group may be tri-substituted in a variety of positions, such as at the 2, 4 and 5 positions. The substituents of a phenyl group that is mono-, di- or tri-substituted may be any type known to those of skill in the art. In certain embodiments, the substituents of a 2,4,5-tri-substituted phenyl group are selected from the group consisting of methyl, methoxy and fluoro. In certain embodiments, $R_2$ of the compound of formula (I) is 2-methoxyphenyl. $R_2$ may be a sugar moiety of any type known to those of skill in the art. In certain embodiments, the sugar is selected from the group consisting of ribosyl, 2'-deoxyribosyl and 2',3'-dideoxyribosyl.

In certain embodiments, at least one of $R_5$ and $R_6$ of the compound of formula (I) is hydrogen. In certain embodiments, both $R_5$ and $R_6$ are hydrogen. $R_5$ and $R_6$ may, in certain embodiments, together form —C(O)—, —$(CH_2)_p$—, —$(CH_2)_qC(O)$— or —$C(O)(CH_2)_r$—, wherein p=1-7 and q and r are independently 1-6.

In the compound of formula (I), at least one of m, n and o is 2 or greater in certain embodiments. For example, m may equal 2.

In certain embodiments, the compound of formula (I) may be further defined as

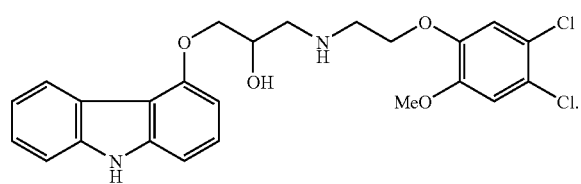 [SMILES: COc1cc(Cl)c(Cl)cc1OCCNCC(O)COc1cccc2[nH]c3ccccc3c12]

In certain embodiments, the compound of formula (I) may be further defined as

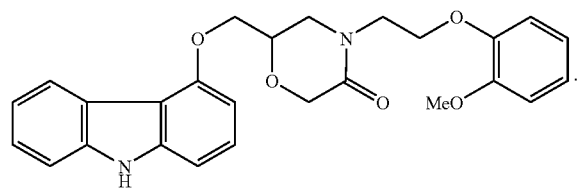 [SMILES: COc1ccccc1OCCN1CC(COc2cccc3[nH]c4ccccc4c23)OCC1=O]

In certain embodiments, the compound of formula (I) may be defined as

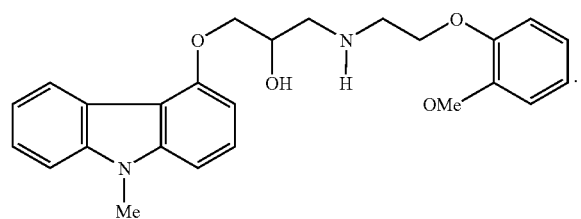 [SMILES: COc1ccccc1OCCNCC(O)COc1cccc2c1c1ccccc1n2C]

In other embodiments, the compound of formula (I) may be further defined as

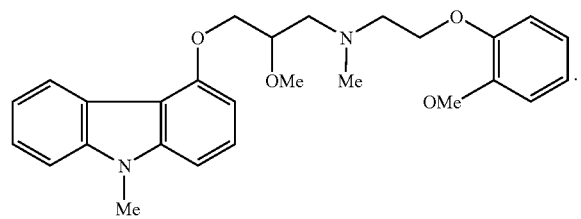 [SMILES: COc1ccccc1OCCN(C)CC(COc1cccc2c1c1ccccc1n2C)OC]

In yet other embodiments, the compound of formula (I) may be further defined as a compound of formula (II):

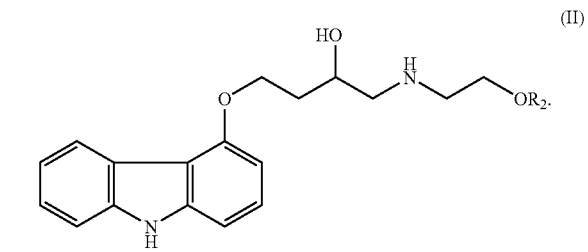

In the compound of formula (II), $R_2$ may be any aryl group known to those of skill in the art. In certain embodiments, $R_2$ is a phenyl group. The phenyl group may optionally be mono-, di- or tri-substituted with a group selected from halogen, lower alkyl and lower alkoxy.

The present invention further contemplates pharmaceutical compositions that comprise a compound of formula (I). Such pharmaceutical compositions may be further defined as a pharmaceutical composition for the treatment of a cardiac condition associated with RyR2. The cardiac condition may be that of any type known to those of skill in the art. In certain embodiments, the cardiac condition is heart failure or arrhythmia.

The present invention also contemplates methods of treating a subject suffering from a cardiac condition associated with RyR2, comprising the step of administering to the subject a RyR2 inhibitor. The cardiac condition associated with RyR2 may be of any type known to those of skill in the art, such as heart failure or arrhythmia. The subject may be a mammal, such as a rodent (e.g., mouse, rat) or human. In such methods, the RyR2 inhibitor may be a compound of claim 1.

In methods of the present invention, SOICR may be inhibited. SOICR may be inhibited about, or at least about 10%, 15%, 20%, 25%, 30%, 35%, 40%, 45%, 50%, 55%, 60%, 65%, 70%, 75%, 80%, 85%, 95%, 99% or about 100%, or any range derivable therein. In methods of the present invention, CICR may be minimally inhibited or not inhibited. In certain embodiments SOICR may be inhibited while CICR is simultaneously minimally inhibited or not inhibited.

As used herein, "ryanodine receptor type 2 inhibitor" or "RyR2 inhibitor" refers to a compound that modulates intracellular calcium release, such as calcium release modulated by the sarcoplasmic reticulum (SR), in cardiac muscle. A RyR2 inhibitor may, for example, modulate calcium release to achieve or maintain intracellular calcium homeostasis in cardiac muscle. A RyR2 inhibitor may suppress store-overload-induced $Ca^{2+}$ release (SOICR). A RyR2 inhibitor may suppress SOICR while minimally inhibiting or not inhibiting $Ca^{2+}$-induced $Ca^{2+}$ release (CICR), as described herein.

As used herein, "minimal inhibition of CICR activity" and variants thereof refers to an extent of inhibition that does not considerably alter the excitation-contraction coupling or the normal function of cardiac cells. Minimal inhibition of CICR activity may refer to, in certain embodiments, about or at most about 5%, 10%, 15%, 20%, 25%, 30%, 35%, or 40% inhibition, or any range derivable therein, of CICR activity.

As used herein, "store-overload-induced $Ca^{2+}$ release" or "SOICR" refers to the spontaneous release of $Ca^{2+}$ by the sarcoplasmic reticulum (SR) under the conditions of $Ca^{2+}$ overload as a result of activation of the ryanodine receptor type 2 (RyR2) channel by SR luminal $Ca^{2+}$. See, e.g., Jiang et al., 2004.

As used herein, "RyR2" refers to the ryanodine receptor type 2 protein, wild-type or mutant, found primarily in heart tissue, but other tissues as well. See, e.g., Nakai et al., 1990; Otsu et al., 1990; Zhao et al., 1999; and Jiang et al., 2004, the contents of each of which are specifically incorporated by reference in their entirety.

As used herein, "a condition associated with RyR2" refers to a disorder or disease that can be treated and/or prevented by modulating RyR2 (ryanodine receptor type 2) that regulates calcium homeostasis in cells. Conditions associated with RyR2 include, for example, cardiac disorders and diseases, which are described in more detail herein.

As used herein, "conditions" comprise diseases, disorders, syndromes, etc. as applicable.

Compounds of the present invention may contain one or more asymmetric centers and thus can occur as racemates and racemic mixtures, single enantiomers, diastereomeric mixtures and individual diastereomers. All possible stereoisomers of the compounds of the present invention are contemplated as being within the scope of the present invention. The chiral centers of compounds of the present invention can have the S- or the R-configuration, as defined by the IUPAC 1974 Recommendations. The present invention is meant to comprehend all such isomeric forms of the compounds of the invention.

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, tartrates, citrates, hydrohalides, phosphates and the like. The term "pharmaceutically acceptable salts" refers to salts prepared from pharmaceutically acceptable non-toxic bases or acids including inorganic or organic bases and inorganic or organic acids, and are described in more detail herein.

Prodrugs and solvates of compounds of the present invention are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1985). Solvates of the compounds of the present invention include, but are not limited to, hydrates.

As used herein, "alkyl" refers to a saturated or unsaturated, straight- or branched-chain radical containing from 1 to 30 carbon atoms. Examples of such radicals include, but are not limited to, methyl, ethyl, n-propyl, isopropyl, n-butyl, isobutyl, sec-butyl, t-butyl, pentyl, iso-amyl, hexyl, decyl and the like. Such radicals may be substituted with groups other than hydrogen, such as aryl, amino, halogen, cyano, thio (e.g., thioether, sulfhydryl), oxy (e.g., ether, hydroxy), alkoxy, carboxy, oxocarboxy and phosphino. "Lower alkyl" refers to an alkyl radical containing 1 to 8 carbon atoms. "Upper alkyl" refers to an alkyl radical containing 9 to 30 carbon atoms. In certain embodiments, one or more specific alkyl radicals may be excluded. It is specifically contemplated that any alkyl radical that may be substituted with a group other than hydrogen may be specifically excluded, in certain embodiments, with such a group. For example, in certain embodiments, an alkyl radical is not substituted with an aryl group. In another example, in certain embodiments, an alkyl radical is not substituted with a phenyl group.

As used herein, "cycloalkyl" refers to a cyclic alkyl radical containing 3-8 carbon atoms. Non-limiting examples of such cycloalkyl radicals include, but are not limited to, cyclopropyl, cyclobutyl, cyclopentyl, cyclohexyl and the like. In certain embodiments, one or more specific alkyl radicals may be excluded.

As used herein, "alkylsulfonate" refers to an alkyl radical, as defined above (e.g., a lower alkyl or an upper alkyl), which comprises a sulfonate ($-SO_3^-$) group. In certain embodiments, one or more specific alkylsulfonate radicals may be excluded.

As used herein, "alkoxy" refers to an alkyl ether radical, wherein "alkyl" is as defined above. Examples of alkyl ether radicals include, but are not limited to, methoxy, ethoxy, n-propoxy, iso-propoxy, n-butoxy, iso-butoxy, sec-butoxy, t-butoxy and the like. "Lower alkoxy" refers to an alkoxy group containing 1 to 8 carbon atoms. In certain embodiments, one or more specific alkyoxy radicals may be excluded.

As used herein, "acyl" refers to an alkylcarbonyl radical, wherein "alkyl" is as defined above. Examples of acyl radicals include, but are not limited to, $-C(O)(CH_2)_nCH_3$, wherein n=0-18, $-C(O)(CH)(CH_3)_2$ and $-C(O)C(CH_3)_3$. In certain embodiments, one or more specific alkyl radicals may be excluded.

As used herein, "aryl" refers to either a carbocyclic aromatic radical or a heterocyclic aromatic radical. Examples of aryl radicals include, but are not limited to, phenyl, naphthyl, indenyl, furyl, thienyl and pyridyl. Such radicals may be substituted with groups other than hydrogen, such as aryl, amino, halogen, cyano, thio (e.g., thioether, sulfhydryl), oxy (e.g., ether, hydroxy), alkoxy, carboxy, oxocarboxy and phosphino. In certain embodiments, one or more specific aryl groups may be excluded.

As used herein, "halogen" refers to fluoro, chloro, bromo, or iodo. In certain embodiments, one or more halogens may be excluded.

As used herein, "sugar" refers to mono-, di- and tri-saccharides such as sucrose, glucose, fructose, ribose, galactose, maltose, and arabinose, and includes deoxy- and dideoxy-forms of sugars. In certain embodiments, one or more sugars may be excluded.

The term "effective," as that term is used in the specification and/or claims (e.g., "an effective amount," means adequate to accomplish a desired, expected, or intended result.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," or "prevention," or any variation of these terms, when used in the claims and/or the specification includes any measurable decrease or complete inhibition to achieve a desired result.

Throughout this application, the term "about" is used to indicate that a value includes the inherent variation of error for the device or the method being employed to determine the value, or the variation that exists among the study subjects. For example, "about" can be within 10%, within 5%, within 1%, or within 0.5%.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

When describing the present invention, all terms not defined herein have their common, art-recognized meanings.

It is contemplated that any embodiment discussed in this specification can be implemented with respect to any compound, method, or composition of the invention, and vice versa.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1: $Ca^{2+}$ induced $Ca^{2+}$ release (CICR), store-overload-induced $Ca^{2+}$ release (SOICR) and triggered arrhythmia.

FIG. 2: Cardiac arrhythmia and sudden death linked to reduced SOICR threshold. This model proposes that the threshold for SOICR is primarily determined by RyR2 (red bar). In the normal SR, the threshold for SOICR is higher than the SR free $Ca^{2+}$ level (blue area) under both resting and stimulated conditions (upper panel). Therefore, there is little or no $Ca^{2+}$ spillover from the normal SR in either the resting or stimulated states. On the other hand, in the abnormal SR the threshold for SOICR is reduced (lower panel). Under resting conditions, the reduced threshold for SOICR is still higher than the resting SR free $Ca^{2+}$ level, so that there is little or no $Ca^{2+}$ spillover. However, under stimulated conditions (catecholamines or stresses), the abnormal SR is abruptly overloaded with $Ca^{2+}$ (orange area). Because of the reduced threshold, SOICR will be more likely to occur during SR $Ca^{2+}$ loading. The resulting SR $Ca^{2+}$ spillover can lead to arrhythmia and sudden death.

DETAILED DESCRIPTION OF THE INVENTION

Figure 3:
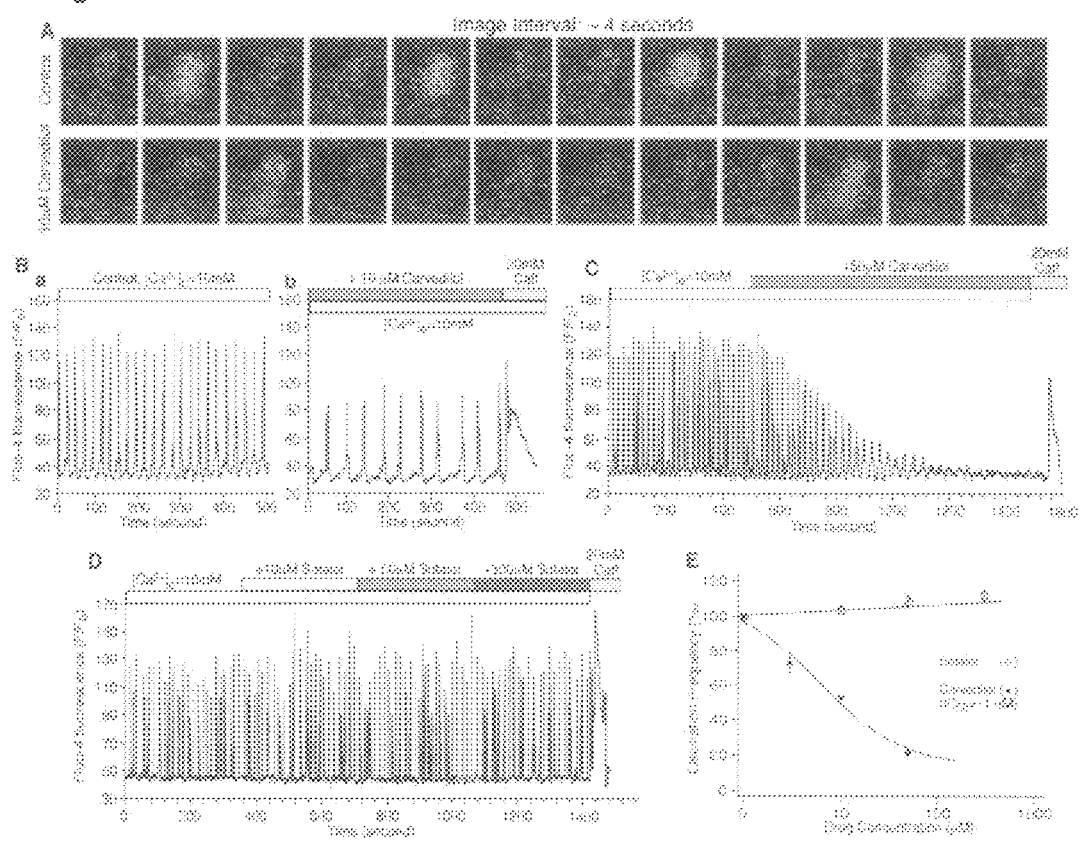
FIG. 3: Carvedilol, but not sotalol, suppresses SOICR in rat ventricular myocytes. Rat ventricular myocytes were loaded with a fluorescent $Ca^{2+}$ indicator, fluo 4-AM, and incubated at a high concentration of external $Ca^{2+}$ (10 mM) to induced SR $Ca^{2+}$ overload and SOICR, which manifests as $Ca^{2+}$ oscillations. Note that carvedilol is able to suppress SOICR with an $IC_{50}$ of ~10 μm while sotalol up to 300 μM has no effect on SOICR.

In general, the present invention provides for novel RyR2 inhibitors, methods of their use in cardiac therapy. For example, these compounds and methods offer treatment for diseases and disorders affected by intracellular calcium imbalance in cardiac muscle. Such diseases and disorders include heart failure and cardiac arrhythmia.

A. RYANODINE RECEPTORS

The contraction of striated muscle is initiated when calcium is released from tubules within the muscle cell known as the sarcoplasmic reticulum (SR). Calcium release channels (ryanodine receptors, "RyR") on the sarcoplasmic reticulum are required for excitation-contraction coupling. These membrane-bound receptors, named after the plant alkaloid ryanodine to which they show high affinity, comprise the major cellular mediators of calcium-induced calcium release (CICR) in animal cells. RyRs are ligand activated channels, and calcium is the important physiological ligand that activates the channels in cardiac muscle during excitation-contraction coupling. A small amount of $Ca^{2+}$ in the cytosol near the receptor will cause it to release even more $Ca^{2+}$, resulting in CICR. Bers, 2002. The calcium-dependence of the RyR channel activity is biphasic such that low cytosolic calcium concentration (μM) activates the channels and high calcium concentration (mM) inactivates the channels. Fill and Copello, 2002. Calcium release from the SR in skeletal muscle cells and heart cells is a key physiological mechanism that controls muscle performance, because increased concentration of calcium in the intracellular cytoplasm causes contraction of the muscle.

B. CARDIAC CONDITIONS AND THERAPY

Cardiac conditions can be either acute or chronic, and either congenital or acquired. The present invention contemplates compounds and methods for the treatment of cardiac conditions. Non-limiting exemplary cardiac conditions include disorders and diseases such as irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof.

Congestive heart failure, also called congestive cardiac failure or simply heart failure, is a condition that can result from any structural or functional cardiac disorder that impairs the ability of the heart to fill with or pump a sufficient amount of blood throughout the body. Causes and contributing factors to congestive heart failure include the following: genetic family history of heart failure, ischemic heart disease/myocardial infarction, infection, anemia, arrhythmia, hypertension and mitral valve disease.

Cardiac arrhythmia is a group of conditions in which the muscle contraction of the heart is irregular or is faster or slower than normal. Some arrhythmias are life-threatening medical emergencies that can cause cardiac arrest and sudden death. Others cause aggravating symptoms, such as an awareness of a different heart beat, or palpitation, which can be annoying. Some are quite small and normal. Sinus arrhythmia is the mild acceleration followed by slowing of the normal rhythm that occurs with breathing. In adults the normal heart rate ranges from 60 beats per minute to 100 beats per minute. The normal heart beat is controlled by a small area in the upper chamber of the heart called the sinoatrial node or sinus node. The sinus node contains specialized cells that have spontaneous electrical activity that starts each normal heart beat. A heart rate faster than 100 beats/minute is considered a tachycardia. A serious variety of arrhythmia is known as fibrillation. The muscle cells of the heart normally function together, creating a single contraction when stimulated. Fibrillation occurs when the heart muscle begins a quivering motion due to a disunity in contractile cell function. Fibrillation can affect the atrium (atrial fibrillation) or the ventricle (ventricular fibrillation); ventricular fibrillation is imminently life-threatening.

1. β-Blockers

A number of pharmacological therapies have been employed to treat heart failure and cardiac arrhythmias. Unfortunately, large clinical trials have recently demonstrated that most of these therapies have little or no survival benefits, and that some of these drugs can even induce arrhythmia and sudden death. Miller, 2003. These disappointing findings indicate that our understanding of the pathogenesis of heart failure and cardiac arrhythmia is incomplete, and clearly point to a pressing need for novel therapeutic approaches and a new generation of anti-arrhythmic drugs.

Most current anti-arrhythmic drugs target cardiac ion channels on the cell surface. Given the negative past experiences, these ion channels are no longer considered to be the prime target for the development of new anti-arrhythmic drugs. Sanguinetti and Bennett, 2003.

β-blockers, the common term for antagonists of β-adrenergic receptors, were originally developed in the 1980's for the treatment of angina and hypertension. Recent large randomized clinical trials have consistently demonstrated that treatment with β-blockers significantly improves cardiac function and reduces sudden cardiac death in patients with heart failure. Foody et al., 2002. This is surprising, because β-blockers, which have a negative inotropic effect on normal myocardium, were once considered to be dangerous and contraindicated for patients with heart failure. The exact mechanisms underlying the beneficial effects of β-blockers are unknown. Barry and Gilbert, 2003.

However, not all β-blockers can reduce the risk of sudden cardiac death. β-Blockers with proven beneficial effects on mortality, such as carvedilol, the only β-blocker approved by the U.S. Food and Drug Administration for the treatment of heart failure, have a high degree of lipophilicity and membrane permeability, while those with no influence on mortality, such as sotalol, are generally hydrophilic and membrane impermeable. Hjalmarson, 2000; Farrell et al., 2002. These observations suggest that the beneficial impact of β-blockers on mortality is likely to be mediated by their non-class effects, probably via intracellular mechanisms.

2. SOICR and RyR2 Inhibition

An increasing body of evidence indicates that intracellular $Ca^{2+}$ homeostasis, which is largely controlled by the sarcoplasmic reticulum (SR) in muscle cells, plays an essential role in the pathogenesis of cardiac arrhythmia. Sanguinetti and Bennet, 2003; Pogwizd and Bers, 2004. Under conditions of SR $Ca^{2+}$ overload, spontaneous SR $Ca^{2+}$ release occurs as a result of activation of the RyR2 channel by SR luminal $Ca^{2+}$, a process referred to herein as store-overload-induced $Ca^{2+}$ release or SOICR (FIG. 1). Jiang et al., 2004.

It appears that SOICR is common in many cardiac settings and may contribute to the enhanced propensity for cardiac arrhythmias. Lakatta, 1992. Indeed, it has recently been shown that the sensitivity for SOICR is increased in failing hearts. Vermeulen et al., 1994; Baartscheer et al., 2003. There is evidence that mutations of the cardiac ryanodine receptor type 2 (RyR2), a key player in the pathogenesis of cardiac arrhythmia, that are associated with cardiac arrhythmias and sudden death also reduce the threshold for SOICR (FIG. 2). Jiang et al., 2004. Therefore, enhanced SOICR is likely to be a unified mechanism underlying cardiac arrhythmias in patients with various cardiac conditions. Thus, suppressing SOICR represents an alternative approach to the treatment of cardiac arrhythmia. Consequently, proteins that govern SR $Ca^{2+}$ homeostasis, such as the RyR2 channel, may be promising targets for new anti-arrhythmic therapies.

A sensible strategy to suppress SOICR is to inhibit the RyR2 channel. However, RyR2 mediates both normal physiological $Ca^{2+}$ release, a process known as $Ca^{2+}$-induced $Ca^{2+}$ release (CICR), as well as abnormal pathological $Ca^{2+}$ release (SOICR) (FIG. 1) (Bers, 2002). Simply blocking the RyR2 channel would thus be detrimental.

Carvedilol is a strong antagonist of β-adrenergic receptors with an $IC_{50}$ of 1-2 nM (Yao et al., 2003), which is ~1,000 fold lower than the concentration required to inhibit the RyR2-mediated SOICR. If the observed favorable impact of carvedilol on survival is indeed attributable to inhibition of RyR2, one would expect that high dosages of carvedilol are necessary for delivering its beneficial effect. Indeed, clinical trials have demonstrated that higher dosages of carvedilol, if tolerated, produce greater benefits, which are independent of β-blockade. Bristow et al., 1996; Okafor et al., 2003; Schwarz et al., 2003. However, high dosages of carvedilol would inevitably produce adverse effects as a result of severe β-blockade. A variety of side effects of carvedilol have been reported. Many patients, especially those with severe heart failure, are intolerant of high dosages of β-blockers, remaining symptomatic and suffering from sudden cardiac death. Ko et al., 2004. This may account for the low rate of absolute reduction in mortality by carvedilol (~7%), although it is the best clinical outcome observed among all the current treatments of heart failure. Miller, 2003.

The present invention addresses that challenge by providing compounds which, in certain embodiments, selectively inhibit SOICR but not CICR. The present invention further comprises assay systems for assessing specifically the effect of a compound on the activity of CICR and SOICR, respectively.

The present invention is based on the recent discovery that RyR2 is a direct target of some β-blockers. Surprisingly, carvedilol, a β-blocker shown to have significant survival benefits, selectively inhibits the channel activity of RyR2, while another β-blocker, sotalol, clinically proven to be ineffective for the treatment of heart failure and cardiac arrhythmia, has absolutely no effect on RyR2. Therefore, the beneficial effects of carvedilol likely arise from its inhibitory effect on RyR2, rather than from its β-blocking activity, which is, in fact, believed to be associated with its various adverse effects. Ko et al., 2004.

C. COMPOUNDS OF THE PRESENT INVENTION: RYR2 INHIBITORS

1. Design

In certain embodiments, the novel RyR2 inhibitors of the present invention inhibit RyR2-mediated SOICR activity. In certain embodiments, the RyR2 inhibitors have a decreased potency in β-blocking activity, as compared to carvedilol. Such compounds with decreased β-blocking activity are expected to be effective in suppressing cardiac arrhythmias, to have less adverse effects, and to be more tolerated by patients, particularly those with severe heart failure.

In the cardiac setting, comparative clinical studies of β-blockers have revealed that the β-blocking activity of carvedilol is unlikely to mediate its beneficial effects (Schwartz et al., 2003), and that the lipophilicity of carvedilol is an important determinant for its survival benefits. In certain embodiments, the novel compounds of the present invention are based on these observations. The rationale for the design of some of the compounds of the present invention is outlined as follows.

Figure 8:
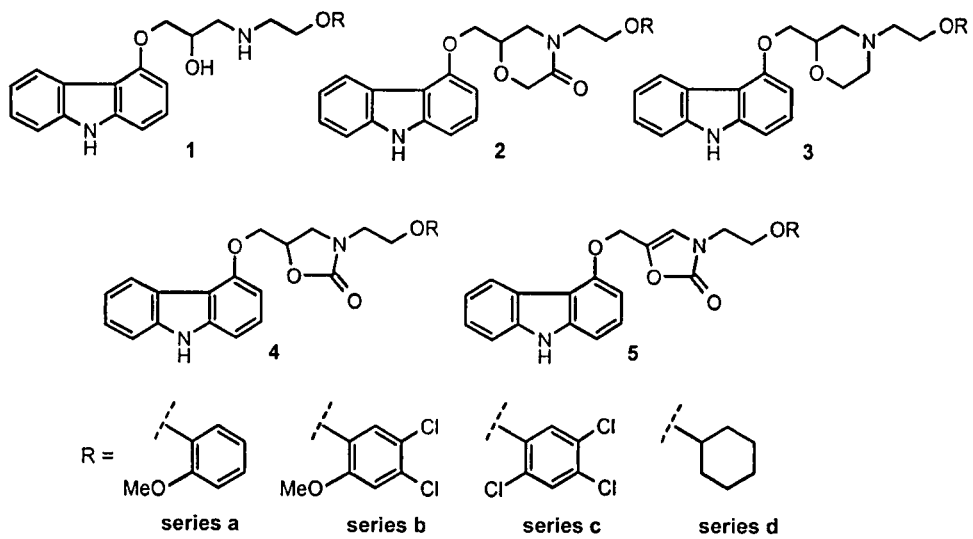
FIG. 8: Structures of certain compounds of the present invention.

Carvedilol (1a) has the following structure (see also FIG. 8):

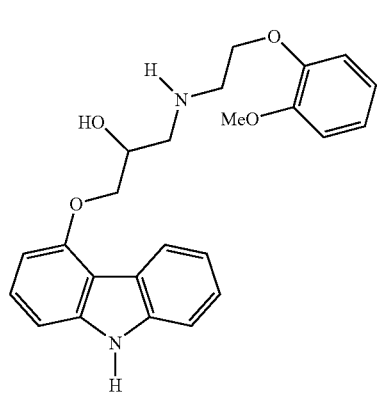

1a

Carvedilol and related compounds which exhibit β-blocking activity require a free hydroxyl and secondary amino group in the bridge between the carbazole and phenyl moieties for β-blockade. Thus, to diminish β-blocking activity, in one embodiment, the OH and NH groups are modified by simple alkylation, or by incorporating them into cyclic morpholine or oxazolinone structures 3a and 5a, respectively, or their homologues.

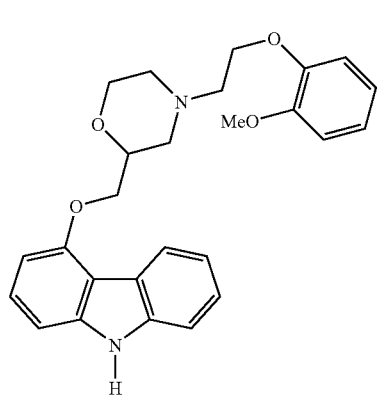

3a

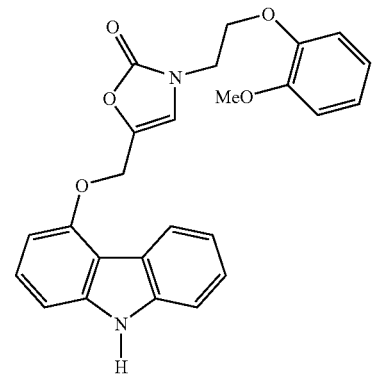

5a

Carvedilol is known to produce 4- and 5-hydroxylated metabolites that possess increased β-blocking activity compared to carvedilol itself. In order to further suppress β-blocking activity, a 4,5-dichlorophenyl derivative 1b may preclude enzymatic aromatic hydroxylation. Furthermore, metabolic demethylation at the 2-position also affords a more active metabolite. Thus, 2,4,5-trichlorophenyl analogue 1c and cyclohexyl derivative 1d may also avoid both unwanted demethylation and oxidation. Alternatively, these positions may be substituted with other halogens or alkyl substituents.

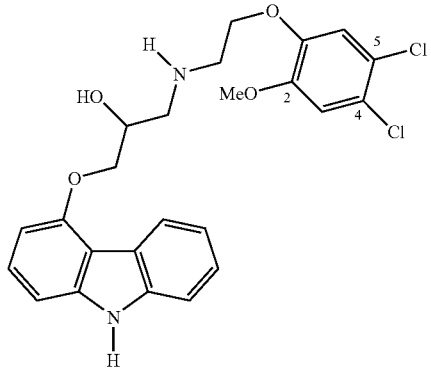

1b

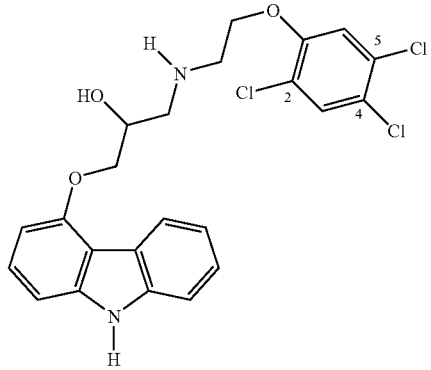

1c

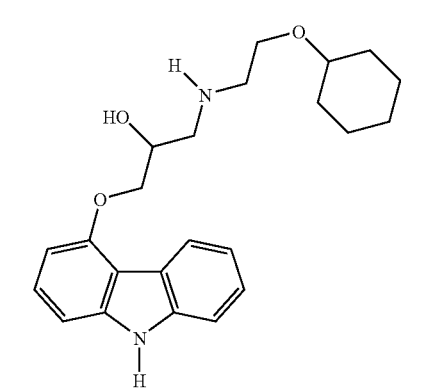

1d

In other embodiments, compounds 3b, 3c, 5b and 5c and their homologues have both cyclization of the OH and NH functions and a chlorinated phenyl moiety.

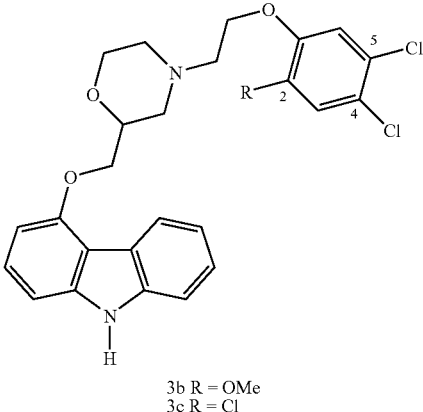

3b R = OMe
3c R = Cl

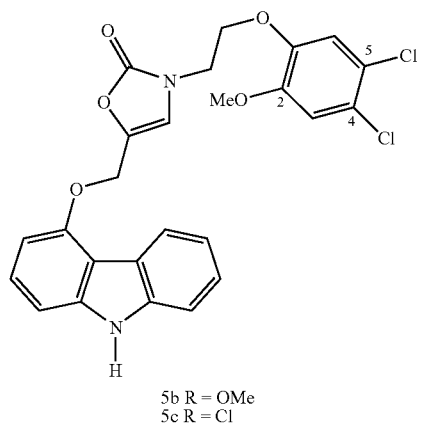

5b R = OMe
5c R = Cl

Compounds 3d and 5d have a morpholine ring, or a oxazolinone ring, or the homologues thereof, and a cyclohexyl ring moiety.

3d

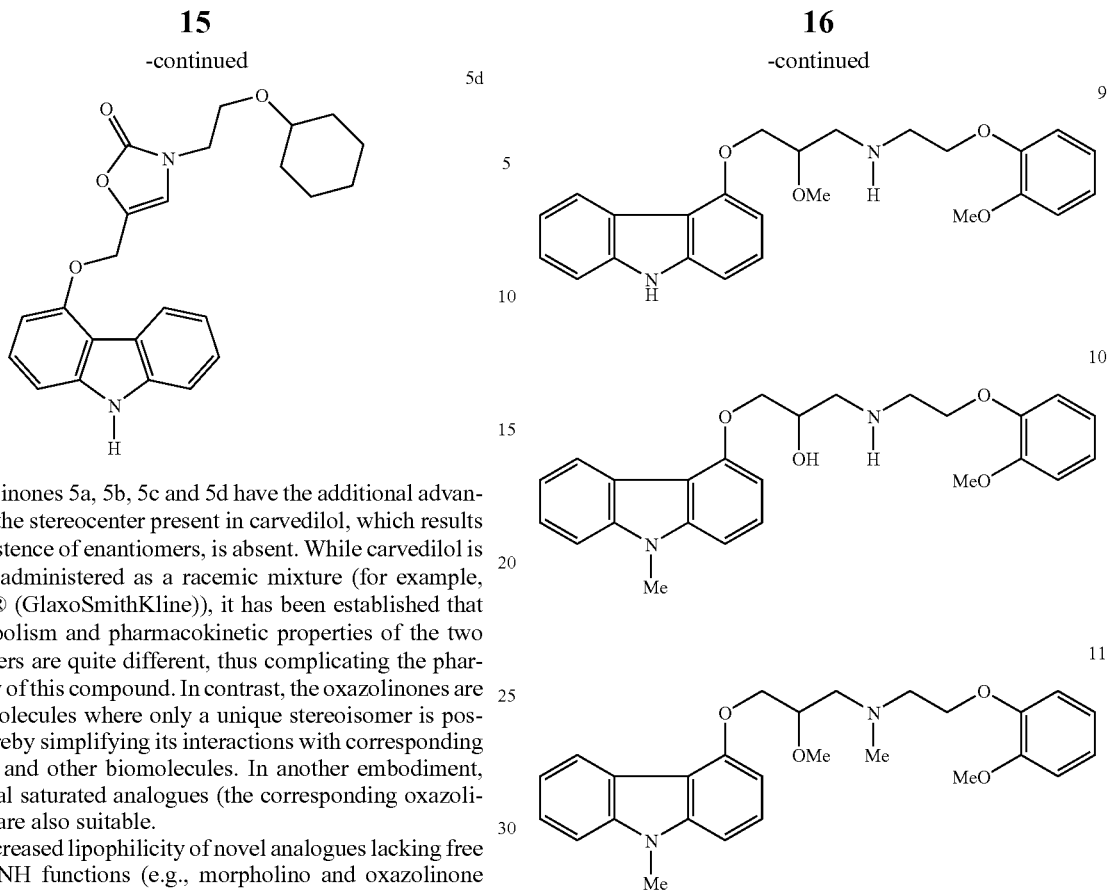

Oxazolinones 5a, 5b, 5c and 5d have the additional advantage that the stereocenter present in carvedilol, which results in the existence of enantiomers, is absent. While carvedilol is typically administered as a racemic mixture (for example, COREG® (GlaxoSmithKline)), it has been established that the metabolism and pharmacokinetic properties of the two enantiomers are quite different, thus complicating the pharmacology of this compound. In contrast, the oxazolinones are achiral molecules where only a unique stereoisomer is possible, thereby simplifying its interactions with corresponding receptors and other biomolecules. In another embodiment, their chiral saturated analogues (the corresponding oxazolidinones) are also suitable.

The increased lipophilicity of novel analogues lacking free OH and NH functions (e.g., morpholino and oxazolinone derivatives) as well as those without methoxyphenyl substituents (e.g., trichloro and cyclohexyl derivatives) result in relatively high concentrations of the compound in target tissue and long residence times. This may diminish the need for an exceptionally high binding affinity for the ryanodine receptor and allows a relatively high $IC_{50}$ (e.g., ≤1 μmolar) as the acceptable threshold.

As an alternative to blocking free OH and NH groups in the linking chain between the carbazole and aryl ether of carvedilol through cyclization to produce compounds such as 2-5, it would also be of interest to selectively block these groups by alkylation. At the same time, the role of the carbazole NH group in binding to a RyR2 receptor may be similarly investigated. Thus, compounds 8-10, wherein each of these functional groups is methylated respectively, as well as the trimethylated (in addition to the existing methylated phenolic hydroxyl group) product 11, where all three functionalities are blocked, can be useful in this context. Compounds 8 and 11 may be easily prepared by controlling the stoichiometry of the alkylation, while standard protecting groups may be used in the selective alkylation of the alcohol and carbazole NH moieties. Methylation may be employed in the first instance, but other alkyl groups can be similarly installed if solubility or other physical properties of these compounds prove incompatible with the SOICR bioassay.

Figure 9:
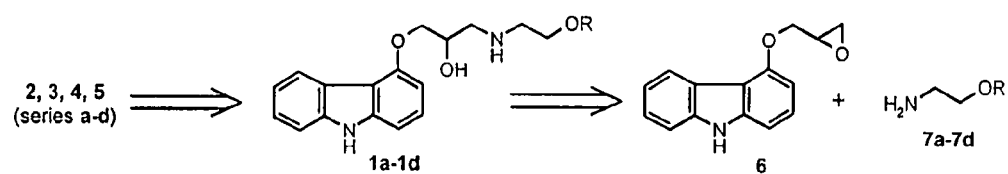
FIG. 9: An exemplary retrosynthetic scheme for preparing certain compounds of the present invention.

The aryl ether moiety appears to play an important role in the bioactivity of certain compounds of the present invention. Compound 1b, for example, displays activity comparable to that of carvedilol (1a) with respect to suppression of SOICR, while the similar trichloro derivative 1c and the cyclohexyl derivative 1d proved inactive. Since metabolic hydroxylation of the 4- and 5-positions of the aryl ether moiety produces metabolites with β-adrenergic activity exceeding that of carvedilol, which is desirable, in certain embodiments, to suppress, it continues to be of interest to introduce substituents that block metabolic activation at these positions. Moreover, the lack of activity of 1c and 1d may be due to poor solubility of these compounds. Thus, modifications of the substituents at the 4- and 5-positions, as well as at the 2-position, in order to correlate bioactivity with solubility and other physical properties such as lipophilicity may be useful (see, e.g., 1e-1h). Further combinations of Me, OMe and F substituents at the 2-, 4- and 5-positions of these and other compounds are also contemplated by the present invention. The modular synthetic approach of Scheme 1 (retrosynthesis, FIG. 9) is applicable for generating these and certain other compounds of the present invention.

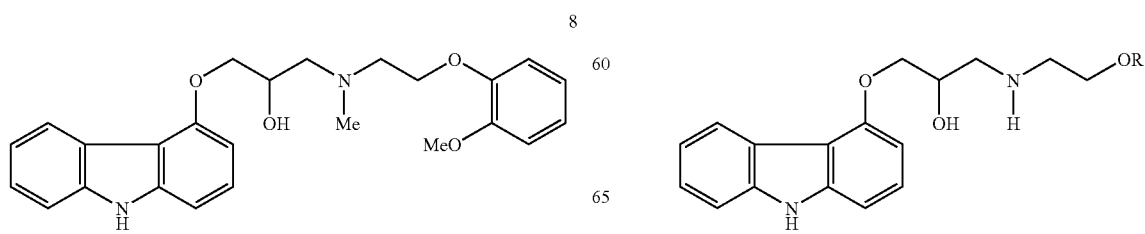

Figure 10:
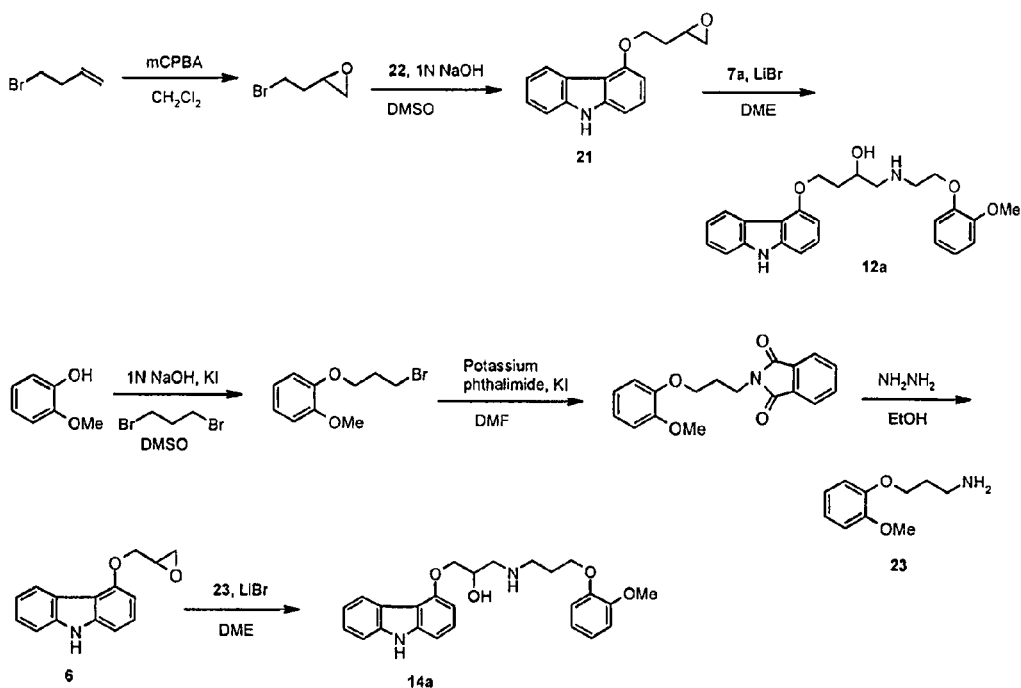
FIG. 10: Exemplary synthetic means for the preparation of certain compounds of the present invention.

Hydroxyl and/or secondary amino groups are, in certain embodiments, required in the linker chain to suppress SOICR, although the effect of their precise location in the chain upon SOICR suppression is not clear. Furthermore, the "normal" positioning of these same functionalities (e.g., as in 1a) is required for the potent β-adrenergic receptor blocking activity of carvedilol. Moreover, recent evidence indicates that the lipophilic carbazole moiety of carvedilol becomes embedded in the cell membrane of the target cells. Butler et al., 2006. Thus, one can postulate that the OH and amino groups interact with a nearby membrane-bound receptor and that the spacing between the carbazole moiety and the key functional groups on the linker chain joining it to the 2-methoxyphenyl substituent is critical in enabling β-blocking activity. Suppression of β-adrenergic inhibition and simultaneous insight into the optimum positioning of these key groups for increased binding to the RyR2 receptor to more efficiently suppress SOICR may be achieved by homologating the connecting chain at several sites. Three differently homologated analogues (12-14) of carvedilol (1a) may be useful in this context (see FIG. 10, Scheme 2).

The known strong interaction of the carbazole moiety of carvedilol with cell membranes (Butler et al., 2006) indicates the requirement for a relatively lipophilic inhibitor. However, limitations to lipophilicity of compounds of the present invention are imposed by, for example, the requirement for solubility of drug candidates in water or other biocompatible solvents such as DMSO. Increased lipophilicity may be achieved by, for example, alkylation, esterification, or amidation of appropriate functionalities in carvedilol (1a) with long-chain alkyl or acyl groups (e.g., 15). The installation of these side chains may be performed similarly to the methylations described earlier for 8-11. If solubility problems become an issue, incorporating surfactant-like side chains instead of, or in addition to, the former substituents (e.g., 16, 17), or increasing the solubility of the compound through conjugation with an appropriate sugar molecule (e.g., ribose in 18) are options. Various applicable sugar structures are well-known to those of skill in the art. In structures 15-18, the side chains or sugar residues are shown attached at the carbazole and phenolic positions, respectively. However, many variations are possible and their attachment to the secondary amine or alcohol groups are contemplated by the present invention. The precise positions for their incorporation may be decided on the basis of, for example, earlier bioassay results of compounds 8-11, which may, in turn, determine the sites where substitution affords optimal bioactivity.

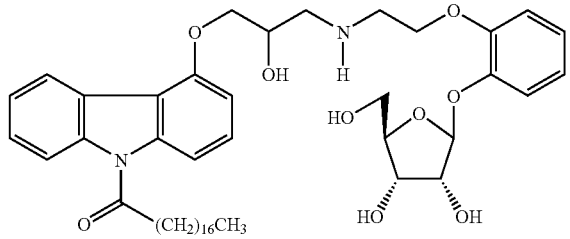

The unsaturated fatty acids EPA (eicosapentenoic acid) and DHA (docosahexenoic acid) have been shown to inhibit RyR2 channel activity. Honen et al., 2003. Thus, hybrid structures where these fatty acids are appended to a carvedilol core structure, as in 24 and 25 may prove to be effective compounds for cardiac therapy. These structures are analogous to the simple stearic acid derivative 15. The EPA and DHA moieties could also be attached to other positions of the carvedilol structure (e.g., 26, 27).

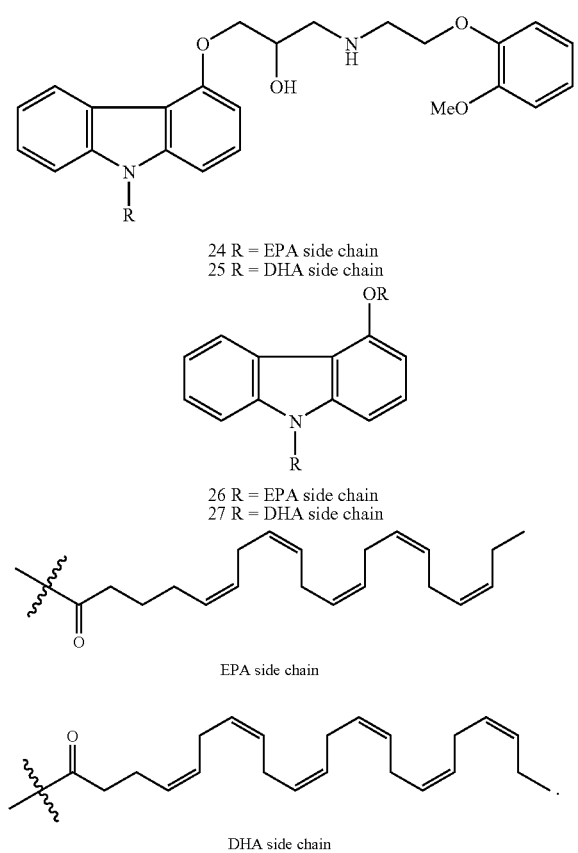

Initial investigations studying RyR2 revealed that 1d, 2b, 2c, 2d, 3a, 3b, 3c, 3d, 4a, 4b and 4d have limited effect in suppressing SOICR. Thus, in certain embodiments, these compounds are excluded.

2. Synthesis

The synthesis of the RyR2 inhibitors may be carried out using well-known synthetic procedures found in the large body of literature which already exists for the preparation of carvedilol and related compounds. The key modifications to carvedilol may be achieved as follows, although many alternative options are also available.

Bridging across the OH and NH groups of 1a to generate morpholine derivatives may require cyclization with chloroacetyl chloride, followed by reduction of the carbonyl group.

The oxazolinone moiety may be installed by carbonylation and cyclization of the corresponding amino alcohol precursor with N,N'-carbonyldi(imidazole) or a dialkyl carbonate, followed by dehydrogenation (e.g., with DDQ). Alternatively, oxidation of the OH group to the ketone, followed by carbonylation of its enol, is expected to afford the desired products. If the corresponding saturated analogues (oxazolidinones) are required, the dehydrogenation step may be omitted in the first approach.

In certain embodiments, the synthesis of certain compounds of the present invention may be carried out as outlined retrosynthetically in Scheme 1 (FIG. 9), which shows that certain compounds of the present invention (e.g., 1b-1d, 2a-2d, 3a-3d, 4a-4-d and 5a-5d, FIG. 8) can be prepared in modular fashion from key intermediates 6 (Kutscher and Reichert, 2001) and 7a-7d. Further details regarding this preparation can be found in the Examples, such as an alternative procedure devised for the preparation of 7d (see Scheme 3, FIG. 11). The modular, converging synthetic approach of Scheme 1 (FIG. 9) permits the facile introduction of further structural modifications to generate additional compounds of the present invention. In certain embodiments, these modifications suppress the β-adrenergic activity of carvedilol while enhancing binding to the RyR2 receptor in order to block SOICR as effectively as possible. Synthetic preparations of certain compounds of the present invention are shown in FIGS. 9-13 (Schemes 1-5).

3. Bioactivity

The bioactivity of the compounds of the present invention may be assessed using various assays in heterologous HEK293 cells and in native rat cardiac myocytes at both the cellular and molecular levels. See, e.g., the Examples below. In certain embodiments, compounds of the present invention show a strong inhibition of RyR2-mediated SOICR, with a minimal impact on CICR and a moderate inhibition of β-adrenergic receptors.

D. PHARMACEUTICAL FORMULATIONS AND ADMINISTRATION THEREOF

Pharmaceutical compositions of the present invention comprise an effective amount of one or more candidate substances or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. Compounds of the present invention may be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject. In certain embodiments, pharmaceutical compositions may comprise, for example, at least about 0.1% of a RyR2 inhibitor. In other embodiments, the RyR2 inhibitor may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

E. COMBINATION THERAPY

In order to increase the effectiveness of a RyR2 inhibitor of the present invention, a RyR2 inhibitor may be combined with traditional drugs. It is contemplated that this type of combination therapy may be used in vitro or in vivo. In a non-limiting example, an anti-arrhythmia agent may be used in combination with a RyR2 inhibitor. The anti-arrhythmia agent may be a β-blocker, such as carvedilol, which may be used in combination with a RyR2 inhibitor of the present invention.

More generally, agents of the present invention would be provided in a combined amount with an effective amount of an anti-arrhythmia agent to better control SR $Ca^{2+}$ release. This process may involve contacting the cell(s) with the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a RyR2 inhibitor is "A" and a second agent, such as an anti-arrhythmia agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effects of Carvedilol and Sotalol on SOICR in Rat Ventricular Myocytes

The effects of carvedilol and sotalol on SOICR in rat ventricular myocytes were assessed. In the experiments shown in FIG. 3, rat ventricular myocytes were loaded with a fluorescent $Ca^{2+}$ indicator, fluo-4, and incubated at a high concentration of extracellular $Ca^{2+}$ (10 mM) to induce SR $Ca^{2+}$ overload and SOICR, which manifests as $Ca^{2+}$ waves/oscillations. These $Ca^{2+}$ oscillations were monitored by a single cell $Ca^{2+}$ imaging technique. As shown in FIG. 3, carvedilol is able to suppress the frequency of SOICR with an $IC_{50}$ of ~10 μM (FIG. 3E), and abolish SOICR at 50 μM (FIG. 3C), while sotalol up to 300 μM has no effect on SOICR (FIGS. 3D and 3E). These findings indicate that RyR2 may mediate the beneficial effect of carvedilol.

Example 2

Effects of Compounds of the Present Invention on SOICR Using a Cellular Assay The impact of each carvedilol derivative of the present invention on SOICR may be examined using a cellular assay. This bioassay takes advantage of the finding that HEK293 cells expressing RyR2 mutants associated with cardiac arrhythmia and sudden death, readily display SOICR at elevated extracellular $Ca^{2+}$. Using this assay the effects of carvedilol and sotalol on SOICR was exampled. Preliminary results show that carvedilol (~10 μM) abolishes SOICR, while sotalol (up to 500 μM) has no significant effect. This assay may be employed to determine the dose-dependent effect of each proposed compound on SOICR.

HEK293 cells may be loaded with a fluorescent $Ca^{2+}$ dye, fura-2-AM. SOICR, which manifests in the form of $Ca^{2+}$ oscillations, is continuously monitored by measuring the fluorescent changes using the single cell $Ca^{2+}$ imaging technique. Cells will be perfused with increasing concentrations (10 nM to 100 μM) of the compound. The frequency and amplitude of $Ca^{2+}$ oscillations under each condition will be determined and analyzed. Compounds that inhibit SOICR are expected to reduce the frequency of $Ca^{2+}$ oscillations, or abolish $Ca^{2+}$ oscillations.

Example 3

Figure 4:
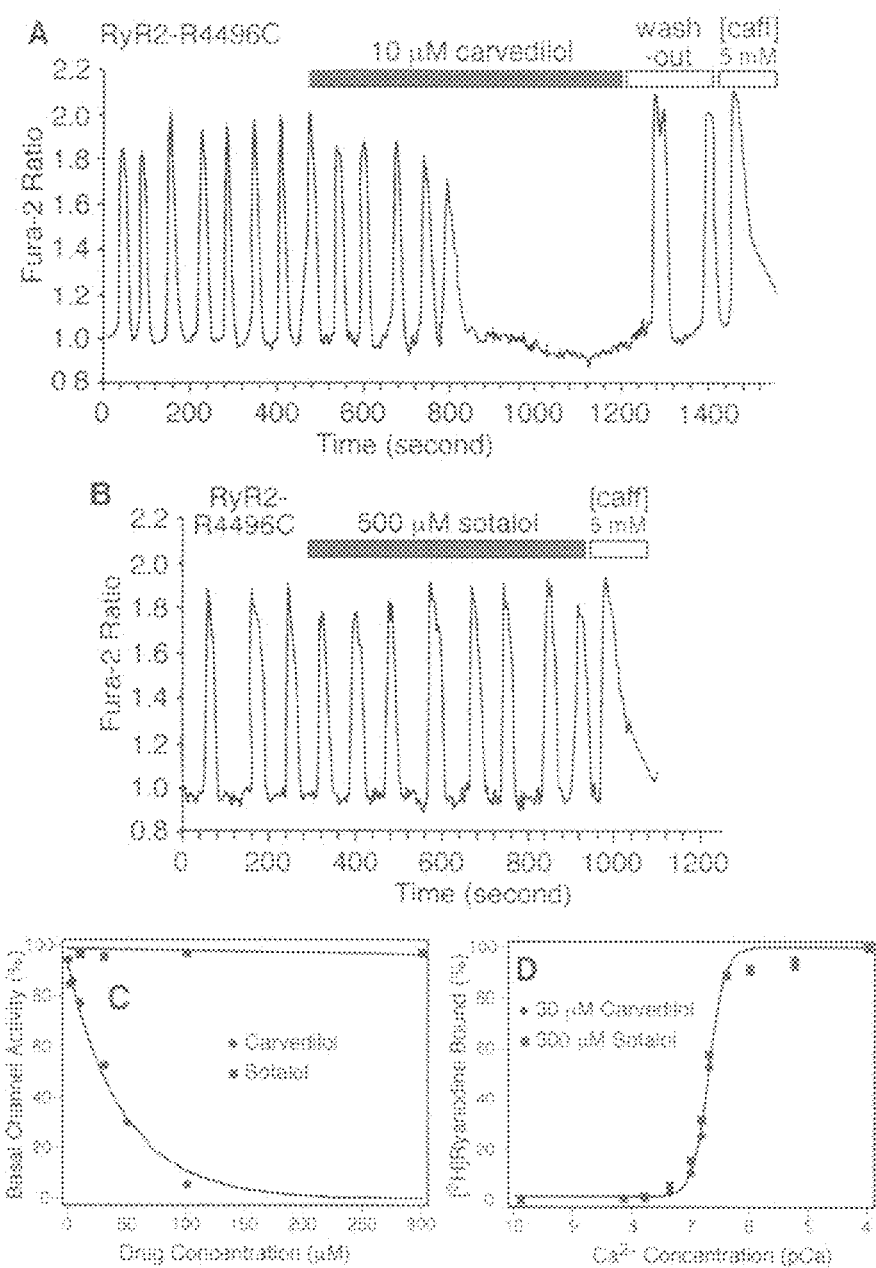
FIG. 4: Effect of carvedilol and sotalol on SOICR, basal activity, and $Ca^{2+}$ dependence of [$^3$H]ryanodine binding. HEK293 cells expressing RyR2-R4496C mutant were loaded with fura 2-AM and perfused with KRH buffer containing 0.5 mM $[Ca^{2+}]_o$ and 10 μM carvedilol (A) or 500 μM sotalol (B). Intracellular $Ca^{2+}$ transients were monitored using single cell $Ca^{2+}$ imaging. Note that carvedilol but not sotalol inhibited SOICR. [$^3$H]Ryanodine binding to cell lysates was carried out at 3 nM $Ca^{2+}$ in the presence of various concentrations of drugs (C) or at various concentrations of $Ca^{2+}$ in the presence of carvedilol or sotalol (D). Note that carvedilol, but not sotalol, inhibited basal channel activity (C). However, both carvedilol and sotalol have no effect on the $Ca^{2+}$ dependence of [$^3$H]ryanodine binding (D).

Examination of the Ability of Compounds of the Present Invention to Suppress the Activity of the RyR2 Channel To determine if the compounds that are capable of suppressing SOICR directly act on RyR2, their effects on the basal channel activity of detergent-solubilized RyR2 may be assessed using [$^3$H]ryanodine binding assay (Jiang et al., 2004). [$^3$H]Ryanodine binding has been widely used as a functional assay for assessing the activity of the RyR2 channel. It has been shown previously that under high salt conditions (500-1000 mM KCl), RyR2 exhibits some basal channel activity even in the absence of $Ca^{2+}$. Interestingly, most of the RyR2 mutations known to cause sudden cardiac death markedly increase the KCl-induced basal activity of the RyR2 channel as revealed by [$^3$H]ryanodine binding in the absence $Ca^{2+}$. More interestingly, this enhanced basal activity of [$^3$H] ryanodine binding to mutant RyR2 channels is strongly suppressed by carvedilol with an $IC_{50}$ of ~30 μM, but not by sotalol (300 μM), indicating that carvedilol suppresses SOICR by affecting the activity of the RyR2 channel (FIG. 4C). These [$^3$H]ryanodine binding studies reveal whether suppression of SOICR by a compound is mediated by inhibition of the RyR2 channel activity.

Figure 5:
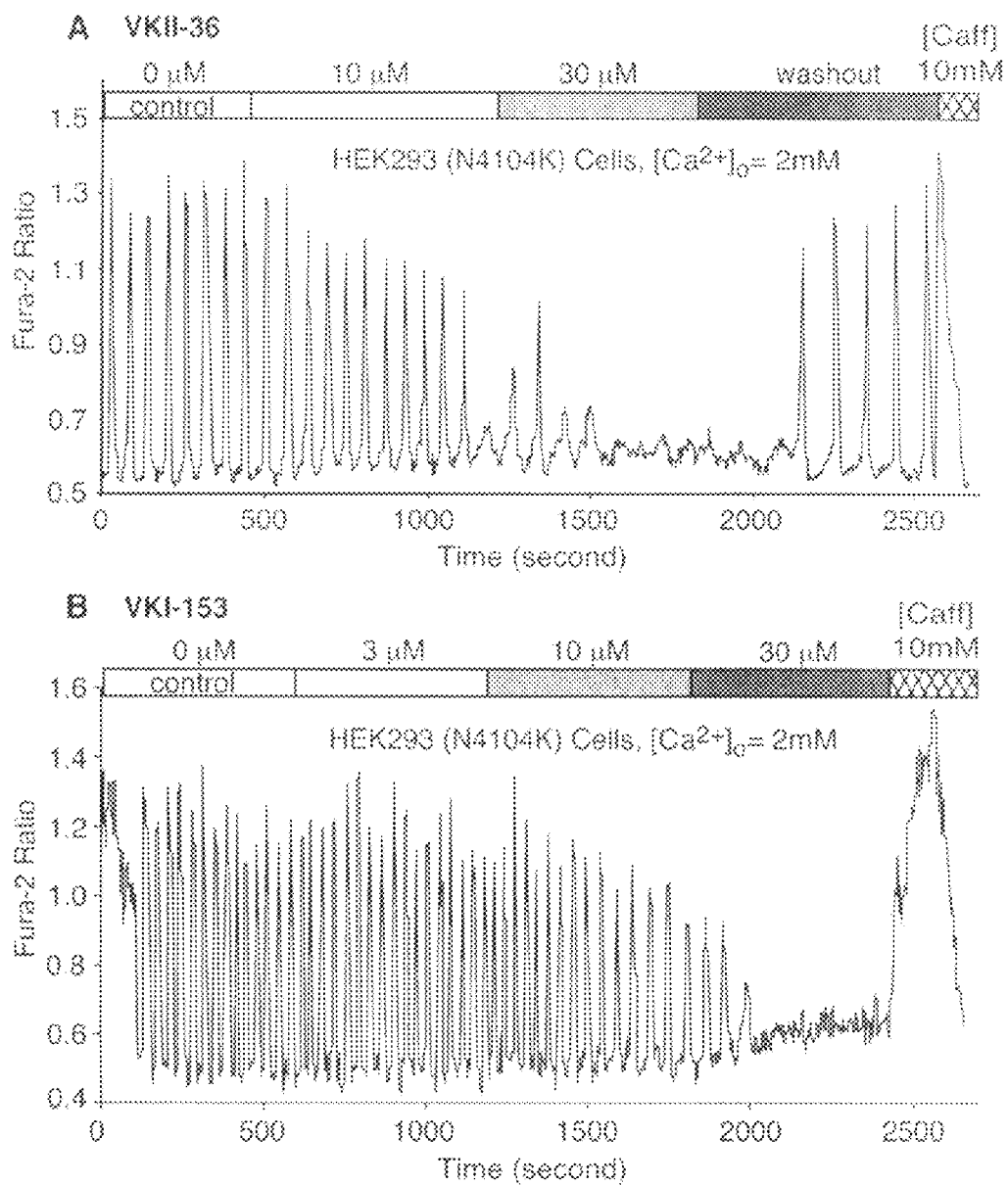
FIG. 5: VK-II-36 (2a) and VK-I-153 (1b) abolish SOICR in HEK293 cells expressing the N4104K RyR2 mutant. HEK293 cells expressing the RyR2—N4104K mutant were loaded with fura 2-AM and perfused with KRH buffer containing 2 mM $[Ca^{2+}]_o$ and various concentrations of VK-II-36 (2a) (panel A) and VK-I-153 (1b) (panel B). Intracellular $Ca^{2+}$ transients were monitored using single cell $Ca^{2+}$ imaging. Note that both compounds inhibited SOICR.

Using these assays, compounds that are capable of suppressing SOICR and basal channel activity of RyR2 expressed in HEK293 cells may be identified. Further verification of whether these identified compounds also work in cardiac cells, the effect of these compounds on SOICR in rat ventricular myocytes may also be determined. Rat ventricular myocytes may be isolated according to the standard procedure using enzymatic digestion. Freshly isolated cells are loaded with a fluorescent $Ca^{2+}$ dye, fluo 4-AM, and bathed at high concentrations of extracellular $Ca^{2+}$ (5-10 mM) to induce SR $Ca^{2+}$ overload and SOICR. The intracellular $Ca^{2+}$ transients as a result of SOICR will be monitored by measuring the fluorescent intensity using a fluorescent microscope. Various concentrations of the selected compounds (10 nM to 100 μM) will be applied and the resulting changes in intracellular $Ca^{2+}$ transients will be determined and analyzed. As SOICR in HEK293 cells expressing RyR2 virtually recapitulates that observed in cardiac cells, compounds that suppress SOICR in HEK293 cells will also inhibit SOICR in cardiac myocytes. In keeping with this view, it has been shown that carvedilol inhibits SOICR in rat ventricular myocytes with an $IC_{50}$ of ~10 μM, and that sotalol (300 μM) does not suppress SOICR at all (FIG. 3). Using the procedures outlined above, the carvedilol derivatives VK-I-153 (1b) and VK-II-36 (2a) were found to suppress SOICR in HEK293 cells at ~30 μM (FIG. 5).

Example 4

Effects of Compounds of the Present Invention on $Ca^{2+}$-Induced $Ca^{2+}$ Release (CICR) Using Rat Cardiac Myocytes The effect of the compounds which inhibit SOICR on CICR may be investigated using freshly isolated rat ventricular myocytes. Rat ventricular myocytes will be isolated and loaded with a fluorescent $Ca^{2+}$ dye, fluo 4-AM. The fluorescent intensity, which reflects the intracellular $Ca^{2+}$ concentration, will be monitored by a fluorescent microscope. Cardiac myocytes will be stimulated by field-depolarizations to trigger SR $Ca^{2+}$ release or CICR in the absence or presence of various concentrations (10 nM to 100 μM) of selected compounds. The amplitude of CICR under each drug concentration will be measured and analyzed. It is important that at their $IC_{50}$ for SOICR, the positive compounds should not have a significant effect on CICR. Otherwise, the compounds would not be useful, as they would interfere with the normal function of RyR2.

Alternatively, the effect of compounds on CICR may be determined using [$^3$H]ryanodine binding. As CICR is dependent, to a large extent, on the sensitivity of the RyR2 channel to activation by $Ca^{2+}$, the effect of a compound on CICR may be determined by assessing the impact of the compound on the sensitivity of the RyR2 channel to $Ca^{2+}$ activation. To this end, [$^3$H]ryanodine binding to the RyR2 channel in a wide range of $Ca^{2+}$ concentrations may be measured. The sensitivity ($EC_{50}$) of [$^3$H]ryanodine binding to RyR2 in the absence and presence of a particular compound may be determined. Using this procedure, carvedilol (30 µM) and sotalol (300 µM) have no significant effect on the sensitivity of RyR2 to $Ca^{2+}$ activation (FIG. 4D).

Example 5

Effects of Compounds of the Present Invention on β-Adrenergic Receptor Signaling The β-blocking effect of the selected compounds may be tested in freshly isolated rat cardiac myocytes. Cardiac cells are isolated, loaded with fluo-4 AM, and bathed in a standard solution containing low $Ca^{2+}$ concentrations (1-2 mM). Cells are then stimulated by a train of short pulses (~10 ms, 0.25 Hz), and the resulting intracellular $Ca^{2+}$ transients will be monitored using a fluorescence microscope. Cells will be pretreated with or without increasing concentrations of a selected compound, followed by the addition of isoproterenol (0.1-1 µM), an agonist of the β-adrenergic receptor known to augment intracellular $Ca^{2+}$ transients. The extent of inhibition on isoproterenol-induced augmentation of $Ca^{2+}$ transients under each condition will be measured and used to determine the $IC_{50}$ of β-blocking activity for each selected compound. Using a procedure similar to that described above, the $IC_{50}$ of β-blocking activity of carvedilol has been reported to be 1-2 nM (Yao et al., 2003). In certain embodiments, compounds of the present invention have little or moderate β-blocking activity.

Figure 6:
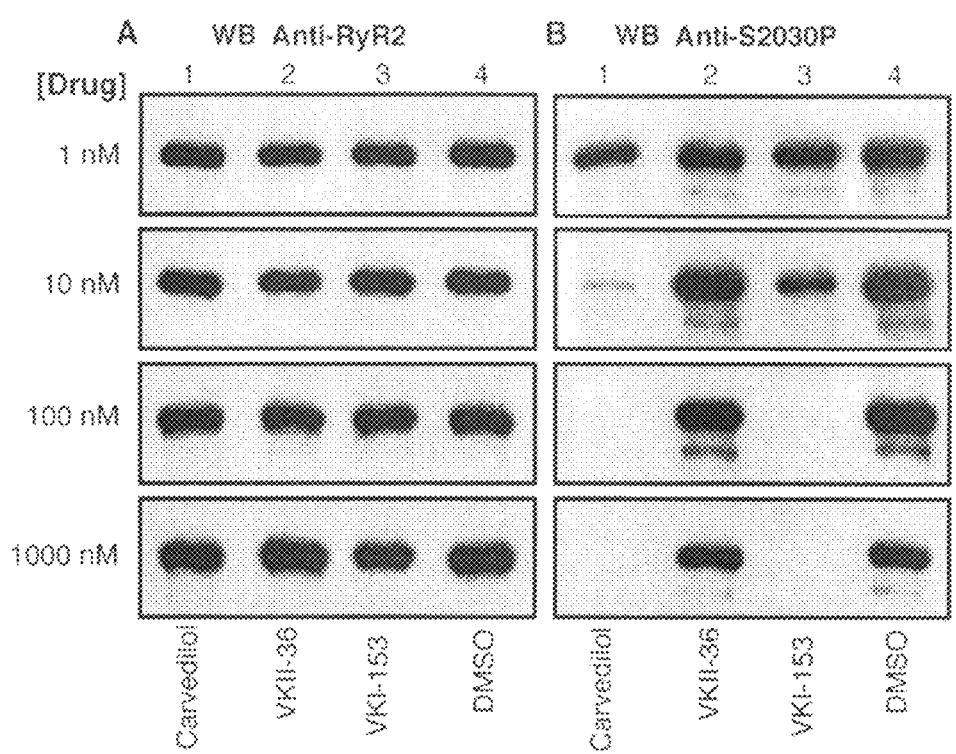
FIG. 6: VK-II-36 is a carvedilol derivative with little β-blocking activity. Rat cardiac myocytes were pre-treated with various concentrations (1-1000 nM) of carvedilol, VK-II-36 (2a), VK-I-153 (1b), or DMSO (control) for 5 min at 37° C. The β-adrenergic receptors were then stimulated by the addition of 200 nM isoproterenol (Iso) in the continued presence of drugs for 30 min at 37° C. Whole cell lysates were prepared and used for Western blotting (WB) analyses. Panel B shows the level of phosphorylation of RyR2 at the PKA-specific site, serine-2030, as determined by using a site- and phospho-specific antibody against the phosphorylated serine-2030 of RyR2 under each condition. The corresponding level of the RyR2 protein under each condition, as assessed by using an anti-RyR2 antibody, is shown in panel A. Note that VK-II-36 (2a), like DMSO, does not block the β-adrenergic receptor at concentrations as high as 1000 nM, while carvedilol and VK-I-153 (1b) completely block the β-adrenergic receptor at 100 nM.

It is known that stimulation of the β-adrenergic receptor (AR) by isoproterenol leads to the activation of the cAMP/protein kinase A (PKA) signaling pathway, which, in turn, results in the phosphorylation by PKA of various protein targets, including the RyR2 channel. RyR2 is specifically phosphorylated at the residue serine-2030 (S2030) upon β-AR stimulation by isoproterenol (Xiao et al., 2005). Hence, alternatively, the β-blocking effects of the selected compounds may be assessed by determining the extent of isoproterenol-induced phosphorylation of RyR2 at S2030. To do this, freshly isolated rat cardiac myocytes are pre-treated with various concentrations of the selected compounds for 5 min, followed by stimulation of the β-AR with 100-200 nM isoproterenol in the continued presence of the selected compounds for 30 min. Whole cell lysates are then prepared and used for determining the level of phosphorylation of RyR2 at S2030 by Western blotting using a site- and phospho-specific antibody against the phosphorylated S2030 site. Using these procedures, the β-blocking effects of carvedilol, VK-I-153 (1b) and VK-II-36 (2a) have been assessed. Our preliminary data indicate that, like DMSO (control), VK-II-36 (2a) has little β-blocking activity as compared to that of carvedilol (FIG. 6).

Example 6

Figure 7:
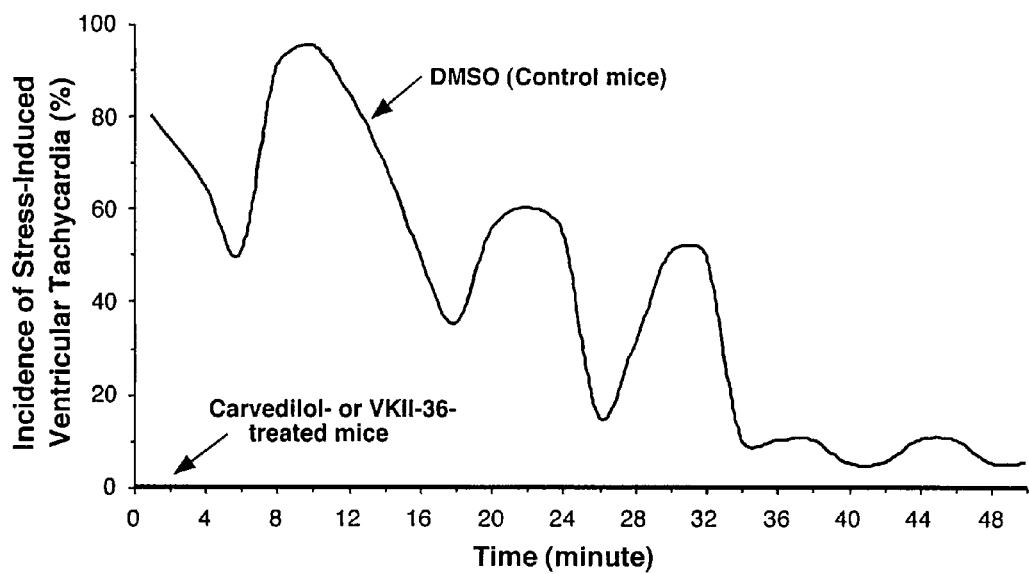
FIG. 7: Carvedilol and VK-II-36 (2a) suppress stress-induced ventricular tachycardia in a mouse model of CPVT. Genetically engineered knock-in (KI) mice harbouring the CPVT mutation, RyR2-R4496C, were treated with various drugs by daily intraperitoneal injection of DMSO, carvedilol or VK-II-36 (2a) (16 mg/kg/day) for 5 days. The KI mice were injected with epinephrine (2 mg/kg) and caffeine (120 mg/kg) on day 6 to induce cardiac arrhythmias. The electrocardiograms (ECG) of the R4496C KI mice were continuously monitored by using telemetric ECG recordings before and after the injection of epinephrine and caffeine. The incidence of ventricular tachycardia (VT) was assessed by determining the duration of VT occurring during a 2-min period (% of time). Note that mice treated with DMSO display a high incidence of VT during the first 30 min after the injection, whereas no VT was observed in mice treated with carvedilol or VK-II-36 (2a).

Effects of Compounds of the Present Invention on Stress-Induced Cardiac Arrhythmia in RyR2 Mutant Mice In order to assess the efficacy of compounds of the present invention in suppressing cardiac arrhythmia at the animal level, genetically engineered knock-in mice were generated harboring RyR2 mutations that are associated with cardiac arrhythmia and sudden death. A heterozygous knock-in mouse line harboring the disease-causing RyR2 mutation, R4496C, has been prepared. Similar to patients who carry the mutation, the R4496C mutant mice are likely prone to stress-induced cardiac arrhythmia and sudden death. If this is the case, this R4496C mouse model may be used to test if compounds of the present invention are able to reduce the incidence of stress-induced cardiac arrhythmia and sudden death. Briefly, mutant mice will be pretreated with or without a positive compound identified above. Epinephrine and caffeine will be injected into the mutant mice to induce cardiac arrhythmia. Telemetric ECG recordings will be used to monitor the cardiac activity at rest and during epinephrine and caffeine perfusion. Using these procedures, experiments have commenced to see whether the selected compounds are able to suppress stress-induced cardiac arrhythmias in our mouse model of CPVT, the R4496C KI mice. Preliminary data indicate that, similar to carvedilol, VK-II-36 (2a) is able to abolish epinephrine and caffeine-induced ventricular tachycardia in the RyR2-R4496C KI mice (FIG. 7).

Example 7

Synthesis of Certain Compounds of the Present Invention (FIGS. 9-13 and Schemes 1-5 Therein)

Figure 11:
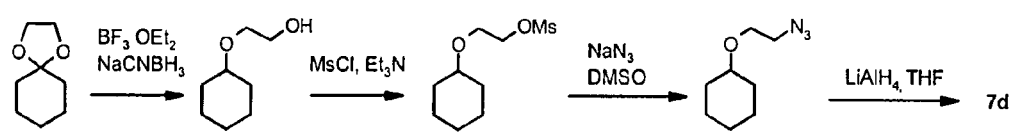
FIG. 11: Exemplary synthetic means for the preparation of compound 7d.
Figure 12:
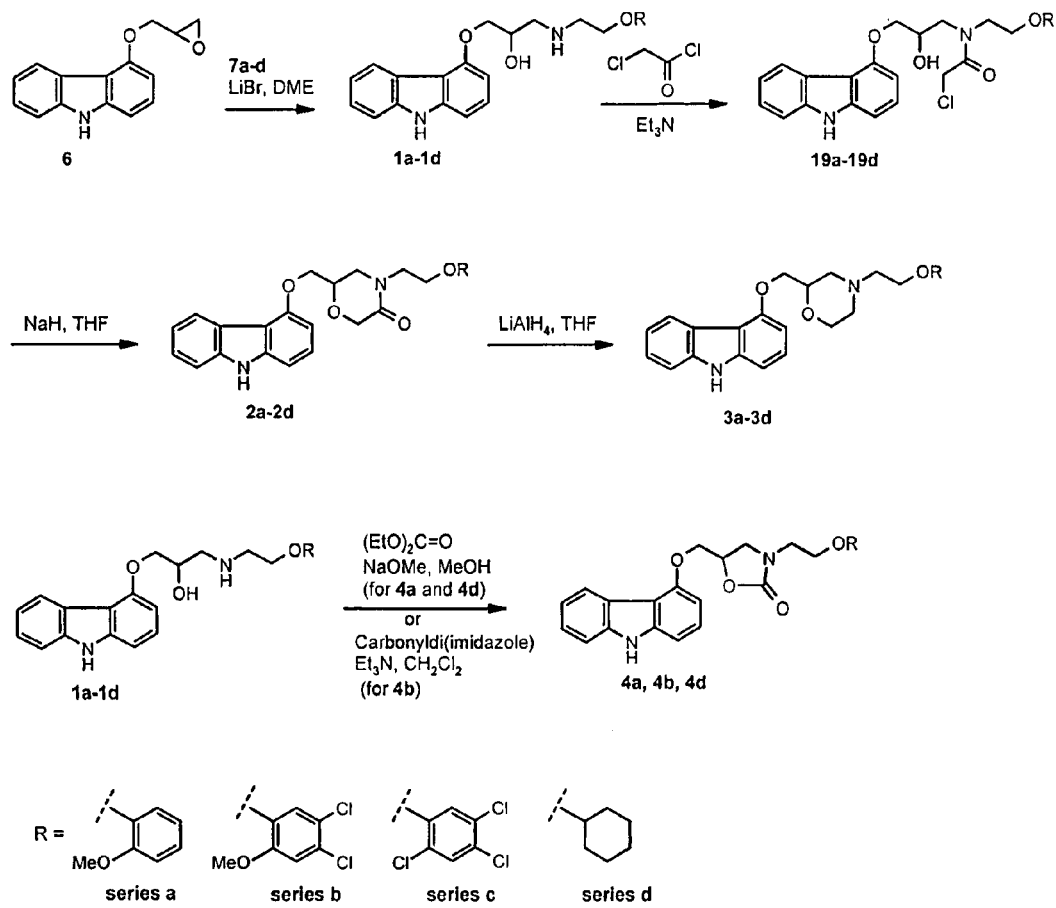
FIG. 12: Exemplary synthetic means for the preparation of certain compounds of the present invention.
Figure 13:
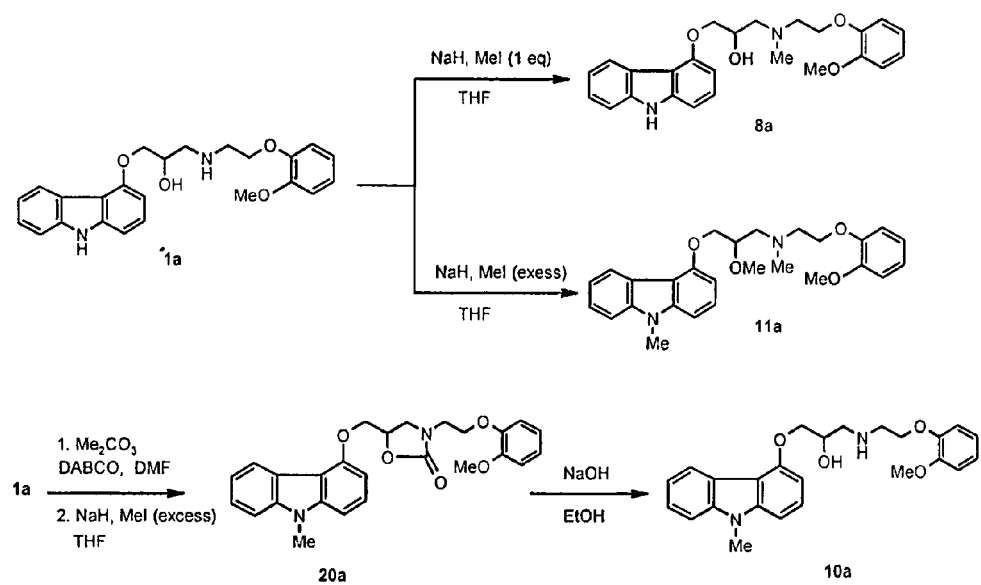
FIG. 13: Exemplary synthetic means for the preparation of certain compounds of the present invention.

All NMR spectra were taken in $CDCl_3$ expect for the $^{13}C$ spectra of 1c and 2c, which were taken in a mixture of $CDCl_3$ and $CD_3OD$. Epoxide 6 was prepared as described in the literature (Kutscher and Reichert, 2001) and amines 7a-7c were prepared by slight modifications of a general method reported in the literature (Liang et al., 2002). Amine 7d was prepared from cyclohexyl 2-hydroxyethyl ether (Srikrishna and Viswajanani, 1995) as shown in Scheme 3 (FIG. 11).

General Procedure for the Preparation of 1b-1d (FIG. 12, Scheme 4):

To a solution of epoxide 6 (1.00 mmol) in anhydrous DME (6 mL) were added amines 7b-7d (2.00 mmol), respectively, and LiBr (catalytic). Each reaction mixture was stirred for 24 h at 50° C. Then the solvent was removed under vacuum, the residues were taken up in ether (10 mL) and washed with water. The aqueous layers were extracted with ether (2×10 mL). The organic layers were washed with brine (25 mL), dried over $Na_2SO_4$, evaporated under reduced pressure and the residues were purified by flash chromatography over silica gel to obtain pure 1b-1d.

1b: yield: 34%; solid; m.p. 149-151° C.; $^1H$ NMR (300 MHz) δ 8.21 (d, J=7.7 Hz, 1H), 8.06 (s, 1H), 7.46-7.14 (m, 4H), 7.06 (d, J=7.7 Hz, 1H), 6.87 (s, 1H), 6.75 (s, 1H), 6.64 (d, J=7.7 Hz, 1H), 4.29-3.91 (m, 5H), 3.57 (s, 3H), 3.10-2.841 (m, 4H); $^{13}C$ NMR (75 MHz) δ 156.22, 150.31, 149.22, 142.39, 140.18, 127.31, 125.44, 123.91, 123.69, 123.32, 119.67, 115.79, 114.44, 113.23, 110.10, 104.73, 101.49, 96.05, 74.31, 70.96, 70.38, 56.69, 54.26, 48.91; mass spectrum, m/z 474 (M+). Exact mass calcd for $C_{24}H_{24}N_2O_4Cl_2$: 474.11131. Found: 474.11232.

1c: yield: 66%; solid; m.p. 146-148° C.; $^1H$ NMR (300 MHz) δ 8.34 (d, J=7.7 Hz, 1H), 7.30-7.13 (m, 4H), 7.02-6.93 (m, 2H), 6.86 (s, 1H), 6.51 (d, J=7.7 Hz, 1H), 4.15-3.96 (m, 5H), 3.07-2.85 (m, 4H); $^{13}C$ NMR (75 MHz) δ 154.86, 153.17, 141.37, 139.12, 131.08, 130.65, 126.26, 124.62, 124.27, 122.50, 122.12, 118.81, 114.90, 112.29, 110.10, 104.05, 100.42, 70.09, 68.58, 68.40, 52.16, 47.96; mass spectrum, m/z 478 (M+). Exact mass calcd for $C_{23}H_{21}Cl_3N_2O_3$: 478.06178. Found: 478.06193.

1d: yield: 61%; viscous oil; $^1H$ NMR (300 MHz) δ 8.28 (d, J=7.7 Hz, 1H), 8.14 (s, 1H), 7.41-7.22 (m, 4H), 7.06 (d, J=7.7 Hz, 1H), 6.68 (d, J=7.7 Hz, 1H), 4.32-4.22 (m, 3H), 3.62-3.59 (m, 2H), 3.27-3.24 (m, 1H), 3.12-3.07 (m, 1H), 3.01-2.78 (m, 4H), 2.00-1.89 (m, 2H), 1.72-1.71 (m, 2H), 1.54-1.49 (m, 1H), 1.39-1.19 (m, 5H); $^{13}C$ NMR (75 MHz) δ 155.24, 141.11, 138.91, 126.79, 125.12, 123.11, 122.66, 119.80, 112.83, 110.19, 104.02, 101.35, 78.10, 70.36, 68.28, 66.59, 52.08, 49.64, 32.37, 25.88, 24.25; mass spectrum, m/z 382 (M$^+$). Exact mass calcd for $C_{23}H_{30}N_2O_3$: 382.22564. Found: 382.22240.

General Procedure for the Preparation of 19a-19d (FIG. 12, Scheme 4):

To an ice-cooled solution of 1a-1d (1.00 mmol), respectively, in CHCl$_3$ were added Et$_3$N (1.50 mmol) and chloroacetyl chloride (1.00 mmol). Each reaction mixture was stirred for 6 h at room temperature and was then quenched with water (10 mL) and extracted with CHCl$_3$ (3×10 mL). The organic layers were washed with saturated NH$_4$Cl solution (25 mL), dried over Na$_2$SO$_4$, evaporated under reduced pressure and the residues were purified by flash chromatography over silica gel to afford 19a-19d. These products were used directly in the preparation of 2a-2d.

General Procedure for the Preparation of 2a-2d (FIG. 12, Scheme 4):

A suspension of NaH (1.10 mmol) in anhydrous THF was cooled to 0° C. Then respective solutions of 19a-19d (1.00 mmol) in THF were added and stirred for 12 h at room temperature. Each reaction mixture was quenched with water (10 mL) and extracted with ethyl acetate (3×10 mL). The organic layers were washed with saturated NH$_4$Cl solution (25 mL), dried over Na$_2$SO$_4$, evaporated under reduced pressure and the residues were purified by flash chromatography over silica gel to obtain pure 2a-2d.

2a: yield: 72%; viscous oil; $^1$H NMR (300 MHz) δ 8.28-8.19 (m, 2H), 7.44-7.06 (m, 6H), 7.01-6.81 (m, 3H), 6.65 (d, J=7.7 Hz, 1H), 4.45-4.21 (m, 7H), 3.96-3.79 (m, 4H), 3.69 (s, 3H); $^{13}$C NMR (75 MHz) δ 167.11, 154.91, 149.77, 148.12, 141.16, 138.90, 126.69, 125.28, 123.11, 122.47, 121.96, 121.02, 119.91, 114.07, 111.97, 110.19, 104.44, 101.34, 72.23, 68.39, 68.00, 67.94, 55.76, 51.25, 47.06; mass spectrum, m/z 446 (M$^+$). Exact mass calcd for $C_{26}H_{26}N_2O_5$: 446.18417. Found: 446.18439.

2b: yield: 92%; viscous oil; $^1$H NMR (300 MHz) δ 8.20 (d, J=7.7 Hz, 1H), 8.09 (s, 1H), 7.44-7.28 (m, 2H), 7.17-7.07 (m, 2H), 6.92 (s, 1H), 6.78 (s, 1H), 6.66 (d, J=7.7 Hz, 1H), 4.48-4.18 (m, 7H), 4.01-3.78 (m, 4H), 3.57 (s, 3H); $^{13}$C NMR (75 MHz) δ 167.15, 154.84, 148.92, 147.30, 141.11, 138.84, 128.46, 126.73, 125.35, 123.46, 122.98, 122.42, 119.91, 115.18, 113.34, 112.94, 110.19, 104.44, 101.34, 72.08, 68.33, 68.26, 67.92, 56.12, 51.32, 46.81; mass spectrum, m/z 514 (M$^+$).

2c: yield: 77%; solid; m.p. 106-108° C.; $^1$H NMR (300 MHz) δ 8.22 (d, J=7.7 Hz, 1H), 8.08 (s, 1H), 7.44-7.18 (m, 5H), 7.09 (d, J=7.7 Hz, 1H), 6.96 (s, 1H), 6.67 (d, J=7.7 Hz, 1H), 4.44-4.19 (m, 7H), 4.02-3.82 (m, 4H); $^{13}$C NMR (75 MHz) δ167.5, 154.3, 153.0, 141.5, 138.6, 131.7, 131.0, 126.2, 125.0, 124.9, 122.3, 122.1, 122.0, 119.0, 114.2, 112.1, 110.0, 104.2, 101.5, 72.0, 68.0, 67.9, 67.6, 50.4, 46.3; mass spectrum, m/z 518 (M$^+$). Exact mass calcd for $C_{25}H_{21}Cl_3N_2O_4$: 518.05669. Found: 518.05990.

2d: yield: 41%; viscous oil; $^1$H NMR (300 MHz) δ 8.24 (d, J=7.7 Hz, 1H), 8.14 (s, 1H), 7.49-7.23 (m, 4H), 7.10 (d, J=7.7 Hz, 1H), 6.68 (d, J=7.7 Hz, 1H), 4.50-4.24 (m, 5H), 3.78 (d, J=Hz, 2H), 3.66 (dd, J=Hz, 4H), 3.28-3.17 (m, 1H), 1.92-1.78 (m, 2H), 1.76-1.42 (m, 3H), 1.32-1.08 (m, 5H); $^{13}$C NMR (75 MHz) δ 166.89, 154.84, 141.21, 138.97, 126.70, 125.28, 123.05, 122.50, 119.84, 112.89, 110.26, 104.45, 101.25, 72.25, 68.25, 67.94, 66.71, 51.07, 47.73, 32.28, 25.84, 24.12; mass spectrum, m/z 422 (M$^+$). Exact mass calcd for $C_{25}H_{30}N_2O_4$: 422.22056. Found: 422.22249.

General Procedure for the Preparation of 3a-3d (FIG. 12, Scheme 4):

To a suspension of LiAlH$_4$ (1.00 mmol) in THF were added 2a-2d (1.00 mmol), respectively, in THF. Each mixture was stirred at room temperature for 3 h and then was quenched with ethyl acetate, followed by the addition of saturated Na$_2$SO$_4$ solution. The crude mixtures were passed through a pad of Celite and washed with ethyl acetate. The filtrates were dried over Na$_2$SO$_4$, evaporated under reduced pressure and the residues were purified by flash chromatography over silica gel to afford 3a-3d.

3a: yield: 60%; viscous oil; IR; $^1$H NMR (300 MHz) δ 8.30 (d, J=7.7 Hz, 1H), 8.09 (s, 1H), 7.46-7.17 (m, 4H), 7.06 (d, J=7.7 Hz, 1H), 6.96-6.84 (m, 4H), 6.66 (d, J=7.7 Hz, 1H), 4.40-4.15 (m, 5H), 4.24-3.93 (m, 1H), 3.91-3.76 (m, 4H), 3.34-3.22 (m, 1H), 3.04-2.84 (m, 3H), 2.58-2.31 (m, 2H); $^{13}$C NMR (75 MHz) δ 155.29, 149.88, 148.40, 141.13, 138.91, 126.75, 125.11, 123.22, 122.67, 121.75, 121.06, 119.77, 114.23, 112.93, 112.16, 110.14, 104.03, 101.33, 74.23, 69.34, 67.04, 66.98, 57.65, 56.76, 55.98, 53.77; mass spectrum, m/z 432 (M$^+$). Exact mass calcd for $C_{26}H_{28}N_2O_4$: 432.20491. Found: 432.20170.

3b: yield: 86%; viscous oil; $^1$H NMR (300 MHz) δ 8.29 (d, J=7.7 Hz, 1H), 8.09 (s, 1H), 7.46-7.13 (m, 3H), 7.06 (d, J=7.7 Hz, 1H), 6.98-6.80 (m, 3H), 6.67 (d, J=7.7 Hz, 1H), 4.37-3.97 (m, 5H), 3.80 (s, 3H), 3.32-3.22 (m, 1H), 3.02-2.84 (m, 3H), 2.58-2.29 (m, 2H); $^{13}$C NMR (75 MHz) δ 155.22, 149.92, 141.07, 138.85, 126.76, 125.14, 123.19, 122.66, 121.93, 121.03, 119.84, 114.47, 112.98, 112.67, 112.12, 110.09, 104.03, 101.40, 74.23, 69.20, 66.50, 57.59, 56.09, 55.95, 53.77; mass spectrum, m/z 466 (M$^+$-Cl+H$^+$). Exact mass calcd for $C_{26}H_{27}ClN_2O_4$: 466.16594. Found: 466.16618.

3c: yield: 66%; viscous oil; $^1$H NMR (300 MHz) δ 8.25 (d, J=7.7 Hz, 1H), 8.07 (s, 1H), 7.46-7.23, (m, 4H), 7.20-7.12 (m, 1H), 7.07 (d, J=7.7 Hz, 1H), 7.00 (s, 1H), 6.67 (d, J=7.7 Hz, 1H), 4.38-4.10 (m, 6H), 4.08-3.86 (m, 2H), 3.46-3.25 (m, 1H), 3.16-2.92 (m, 2H), 2.74-2.48 (m, 2H); $^{13}$C NMR (75 MHz) δ 155.17, 153.32, 141.04, 138.83, 131.33, 131.03, 126.78, 125.17, 124.81, 123.08, 122.61, 122.29, 119.76, 115.08, 112.94, 110.12, 104.06, 101.41, 73.95, 69.06, 67.78, 66.82, 57.16, 56.56, 53.77; mass spectrum, m/z 504 (M$^+$). Exact mass calcd for $C_{25}H_{23}Cl_3N_2O_3$: 504.07743. Found: 504.07574.

3d: yield: 60%; viscous oil; $^1$H NMR (300 MHz) δ 8.31 (d, J=7.7 Hz, 1H), 8.11 (s, 1H), 7.46-7.20 (m, 4H), 7.06 (d, J=7.7 Hz, 1H), 6.66 (d, J=7.7 Hz, 1H), 4.38-4.16 (m, 3H), 4.02-3.81 (m, 2H), 3.66 (t, J=6.15 Hz, 2H), 3.28-3.17 (m, 2H), 2.92-2.83 (m, 1H), 2.72-2.64 (m, 1H), 2.44-2.25 (m, 2H), 1.96-1.83 (m, 2H), 1.78-1.62 (m, 2H), 1.55-1.48 (m, 1H), 1.36-1.14 (m, 5H); $^{13}$C NMR (75 MHz) δ 155.29, 141.07, 13.86, 126.76, 125.09, 123.26, 122.73, 119.77, 112.96, 110.06, 103.92, 101.33, 74.18, 69.35, 67.02, 65.50, 58.75, 56.88, 53.85, 32.38, 29.83, 25.90, 24.35; mass spectrum, m/z 408 (M$^+$-C$_2$H$_2$). Exact mass calcd for $C_{23}H_{30}N_2O_3$: 408.24129. Found: 408.24147.

Preparation of 4a (FIG. 12, Scheme 4):

A solution of carvedilol 1a (50 mg, 0.13 mmol) in methanol (3 mL) was added to sodium methoxide, prepared by adding freshly cut sodium (6.0 mg, 0.25 mmol) to 2 mL of methanol. Then diethyl carbonate (29 mg, 0.25 mmol) was added and the mixture was refluxed for 12 h. The solvent was removed and the residue was partitioned between water and ethyl acetate. The aqueous layer was extracted with ethyl acetate and the combined organic layers were dried over Na$_2$SO$_4$, concentrated and the residue was purified by flash chromatography over silica gel to afford 4a: yield: 65%; solid; m.p. >300° C.; $^1$H NMR (300 MHz) δ 8.16 (d, J=7.7 Hz, 1H), 7.46-7.19 (m, 4H), 7.09 (d, J=7.7 Hz, 1H), 6.98-6.79 (m, 4H), 6.64 (d, J=7.7 Hz, 1H), 5.13-4.99 (m, 1H), 4.48-4.32 (m, 2H), 4.28-4.14 (m, 3H), 4.07-3.98 (m, 1H), 3.88-3.72 (m, 2H), 3.68 (s, 3H); $^{13}$C NMR (75 MHz) δ 158.38, 154.53, 149.57, 147.68, 141.38, 139.13, 126.31, 124.95, 122.69, 122.12, 122.04, 120.95, 119.22, 114.07, 112.21, 111.97, 110.24, 104.57, 100.51, 71.85, 68.04, 67.86, 55.64, 43.93; mass spectrum, m/z 432 (M$^+$). Exact mass calcd for $C_{25}H_{24}N_2O_5$: 432.16852. Found 432.16719.

Preparation of 4b (FIG. 12, Scheme 4):

To a solution of 1b (40 mg, 0.84 mmol) in 3 mL of $CH_2Cl_2$ were added $Et_3N$ (0.17 mL, 1.26 mmol) and carbonyldi(imidazole) (68 mg, 0.42 mmol). The mixture was stirred at room temperature for 10 h. It was then diluted with $CH_2Cl_2$, washed with saturated $NH_4Cl$ solution and water. The aqueous layer was extracted with $CH_2Cl_2$, dried over $Na_2SO_4$, concentrated and the residue was purified by flash chromatography over silica gel to afford 4b: yield: 65%; solid; m.p. 104-106° C.; $^1$H NMR (300 MHz) δ 8.12-8.05 (m, 2H), 7.44-7.20 (m, 4H), 7.13 (d, J=7.7 Hz, 1H), 6.83 (d, J=7.7 Hz, 1H), 5.08-5.02 (m, 1H), 4.43-4.39 (m, 2H), 4.14-3.04 (m, 4H), 3.85-3.62 (m, 2H), 3.52 (s, 3H); $^{13}$C NMR (75 MHz) δ 157.61, 154.40, 148.53, 146.85, 139.69, 137.45, 128.16, 126.83, 124.92, 124.59, 123.45, 123.38, 115.47, 114.76, 113.80, 112.93, 107.87, 105.89, 71.33, 68.53, 68.31, 56.03, 48.64, 43.82; mass spectrum, m/z 500 (M$^+$). Exact mass calcd for $C_{25}H_{22}Cl_2N_2O_5$: 500.09058. Found: 500.09355.

Preparation of 4d (FIG. 12, Scheme 4):

A solution of 1d (100 mg, 0.261 mmol) in methanol (6 mL) was added to sodium methoxide, prepared by adding freshly cut sodium (12 mg, 0.52 mmol) to 2 mL of methanol. Then diethyl carbonate (62 mg, 0.52 mmol) was added and the mixture was refluxed for 12 h. The solvent was removed and the residue was partitioned between water and ethyl acetate. The aqueous layer was extracted with ethyl acetate and the combined organic layers were dried over $Na_2SO_4$, concentrated and the residue was purified by flash chromatography over silica gel to afford 4d: yield: 41%; solid; m.p. 146-148° C.; $^1$H NMR (300 MHz) δ 8.22-8.14 (m, 2H), 7.45-7.19 (m, 4H), 7.10 (d, J=7.7 Hz, 1H), 6.66 (d, J=7.7 Hz, 1H), 5.08-4.98 (m, 1H), 4.46-4.36 (m, 2H), 4.08-4.00 (m, 1H) 3.94-3.83 (m, 2H), 3.68-3.45 (m, 3H), 3.24-3.16 (m, 1H), 1.85-1.39 (m, 6H), 1.28-1.04 (m, 4H); $^{13}$C NMR (75 MHz) δ 157.82, 154.73, 71.24, 68.17, 66.52, 48.80, 44.80, 32.18, 25.79, 24.00; mass spectrum, m/z 408 (M$^+$). Exact mass calcd for $C_{24}H_{28}N_2O_4$: 408.20491. Found: 408.20274.

Preparation of 8a and 11a (FIG. 13, Scheme 5):

A suspension of NaH (60% in oil) (10 mg, 0.25 mmol) in anhydrous THF was cooled to 0° C. Then a solution of carvedilol 1a (100 mg, 0.246 mmol) in THF was added and the mixture was stirred for 20 min at the same temperature. Methyl iodide (35 mg, 0.25 mmol) was added and stirring was continued for 4 h at room temperature. The reaction mixture was quenched with water (10 mL) and extracted with ethyl acetate (3×10 mL). The organic layer washed with saturated $NH_4Cl$ solution (25 mL), dried over $Na_2SO_4$, evaporated under reduced pressure and the residue was purified by flash chromatography over silica gel to afford 8a: yield: 54%; viscous oil; $^1$H NMR (300 MHz) δ 8.29-8.20 (m, 2H), 7.41-7.31 (m, 3H), 7.28-7.26 m, 1H), 7.06 (d, J=8.1 Hz, 1H), 6.93-6.87 (m, 4H), 6.66 (d, J=8.1 Hz, 1H), 4.36-4.21 (m, 5H), 3.78 (s, 3H), 3.27-3.13 (m, 4H), 2.72 (s, 3H); $^{13}$C NMR (75 MHz) δ 154.94, 149.71, 147.63, 140.97, 138.75, 126.70, 125.00, 122.87, 122.47, 122.11, 120.91, 119.65, 114.32, 112.68, 111.91, 110.09, 103.99, 101.25, 69.88, 66.11, 66.04, 61.18, 56.39, 55.71, 43.04; mass spectrum, m/z 420 (M$^+$). Exact mass calcd for $C_{25}H_{28}N_2O_4$: 420.20491. Found: 420.20380.

A suspension of NaH (60% in oil) (0.098 g, 2.5 mmol) in anhydrous THF (6 mL) was cooled to 0° C. Then a solution of carvedilol 1a (0.100 g, 0.246 mmol) in THF (2 mL) was added and the mixture was stirred for 20 min. at the same temperature. Methyl iodide (0.524 g, 3.69 mmol) was added and stirring was continued for 4 h at room temperature. The reaction mixture was quenched with water (10 mL) and extracted with ethyl acetate (3×10 mL). The organic layer washed with saturated $NH_4Cl$ solution (25 mL), dried over $Na_2SO_4$, evaporated under reduced pressure and the residue was purified by flash chromatography over silica gel to afford 11a: yield: 49%; viscous oil; $^1$H NMR (300 MHz) δ 8.22 (d, J=8.2 Hz, 1H), 7.45-7.39 (m, 3H), 7.14-6.71 (m, 3H), 6.99-6.67 (m, 4H), 4.68-4.28 (m, 7H), 4.06-3.96 (m, 1H), 3.83 (s, 3H), 3.77-3.54 (m, 10H); $^{13}$C NMR (75 MHz) δ 154.53, 150.12, 146.31, 142.63, 140.41, 126.83, 125.13, 123.99, 122.69, 121.87, 121.23, 119.39, 116.65, 111.97, 108.33, 102.65, 101.47, 74.25, 66.89, 65.34, 64.81, 64.68, 56.74, 55.64, 54.33, 29.48; mass spectrum, m/z 448 (M$^+$). Exact mass calcd for $C_{27}H_{32}N_2O_4$: 448.2362. Found: 448.23538.

Preparation of 10a (FIG. 13, Scheme 5):

To a solution of carvedilol 1a (50 mg, 0.12 mmol) in dimethyl carbonate (4 mL) and DMF (1 mL) was added DABCO (2 mg) and the mixture was heated at 95° C. for 18 h. Then the reaction mixture was partitioned between ether and water. The ether layer washed with water and brine, dried over $Na_2SO_4$ and evaporated under reduced pressure. The residue was purified by column chromatography to give 20a (41 mg, 75%) as an oil. The product 20a was methylated as in the case of 11a. The methylated product was dissolved in ethanol, 2 N NaOH was added and the mixture was refluxed for 6 h. Then ethanol was removed and the residue was taken up in ethyl acetate and washed with 1 M HCl. The aqueous layer was extracted with ethyl acetate and the combined organic layers were washed with water and brine, dried over $Na_2SO_4$ and evaporated under reduced pressure. The residue was purified by flash chromatography over silica gel to afford 10a (38 mg, 67%) as a solid.

10a: m.p. 130-132° C.; $^1$H NMR (300 MHz) δ 8.30 (d, J=8.2 Hz, 1H), 7.48-7.36 (m, 3H), 7.24 (dd, J=5.13, 12.8 Hz, 1H), 7.06 (d, J=8.2 Hz, 1H), 6.98-6.88 (m, 4H), 6.70 (d, J=8.2 Hz, 1H), 4.36-4.22 (m, 3H), 4.17 (t, J=5.1 Hz, 2H), 3.85 (s, 3H), 3.84 (s, 3H), 3.18-2.99 (m, 4H), 2.72 (br.s, 1H); $^{13}$C NMR (75 MHz) δ 155.31, 149.88, 148.34, 142.67, 140.39, 126.60, 124.95, 123.07, 122.16, 121.81, 121.04, 119.33, 114.37, 112.09, 112.01, 108.06, 101.93, 101.05, 70.45, 68.97, 68.57, 55.95, 52.07, 48.84, 29.44; mass spectrum, m/z 420 (M$^+$). Exact mass calcd for $C_{25}H_{28}N_2O_4$: 420.20491. Found: 420.20851

Preparation of Epoxide 21 (FIG. 10, Scheme 2):

To a cold solution of 1-bromo-3-butene (1.00 g, 7.41 mmol) in $CH_2Cl_2$ was added mCPBA (0.955 g, 5.55 mmol) and the mixture was stirred at room temperature for 8 h. A second portion of mCPBA (0.955 g, 5.55 mmol) was added and stirring was continued overnight. The reaction mixture was diluted with $CH_2Cl_2$ and washed successively with 10% aqueous sodium sulfite and saturated $NaHCO_3$. The organic layer was dried over $Na_2SO_4$, concentrated and the residue was purified by flash chromatography over silica gel to afford the corresponding bromoepoxide (0.637 g, 57%) as a liquid.

To a solution of 4-hydroxycarbazole, 22 (0.300 g, 2.42 mmol) in DMSO (1 mL) were added the above bromoepoxide (0.546 g, 2.90 mmol) and 1 N NaOH (0.097 g, 2.42 mmol). The reaction mixture was stirred for 24 h at 60° C. Then it was cooled to 20° C. and diluted with 25 mL of water and extracted with ethyl acetate (3×20 mL). The combined organic layers were washed with brine, dried ($Na_2SO_4$) and concentrated. The residue was purified by flash chromatography over silica gel to afford epoxide 21 (0.254 g, 61%) as a liquid.

Preparation of 12a and 14a (FIG. 10, Scheme 2):

To a solution of epoxide 21 or 6 (1.00 mmol) in anhydrous DME (6 mL) were added amine 7a or 23 (2.00 mmol), respectively, and LiBr (catalytic). The reaction mixtures were stirred for 24 h at 60° C. After removal of the solvent under vacuum, the residues were taken up in ether (10 mL) and washed with water. The aqueous layers were extracted with ether (2×10 mL). The combined organic layers were washed with brine (25 mL), dried over $Na_2SO_4$, evaporated under reduced pressure and the residues were purified by flash chromatography over silica gel to obtain pure 12a or 14a as liquids.

12a: yield: 73%; $^1$H NMR (300 MHz) δ 8.29 (d, J=7.7 Hz, 1H), 8.16 (s, 1H), 7.43-7.30 (m, 3H), 7.26-7.19 (m, 1H), 7.04 (d, J=8.2 Hz, 1H), 6.96-6.82 (m, 4H), 6.71 (d, J=8.2 Hz, 1H), 4.42 (t, J=6.15 Hz, 2H), 4.12 (t, J=5.13 Hz, 2H), 4.08-4.02 (m, 2H), 3.88-3.79 (m, 4H), 3.13-2.93 (m, 3H), 2.72-2.65 (m, 1H), 2.27-2.05 (m, 2H); $^{13}$C NMR (75 MHz) δ 155.55, 149.74, 148.30, 141.11, 138.89, 126.85, 125.00, 123.04, 122.79, 121.78, 121.09, 119.68, 114.19, 112.71, 111.97, 110.15, 103.65, 101.27, 69.34, 67.04, 65.07, 55.92, 55.26, 48.54, 34.78; mass spectrum, m/z 420 ($M^+$). Exact mass calcd for $C_{25}H_{28}N_2O_4$: 420.20491. Found: 420.20655.

14a: yield: 49%; $^1$H NMR (300 MHz) δ 8.29-8.24 (m, 2H), 7.42-7.28 (m, 2H), 7.22-7.18 (m, 1H), 7.06 (d, J=8.2 Hz, 1H), 6.96-6.82 (m, 4H), 6.65 (d, J=8.2 Hz, 1H), 4.39-4.09 (m, 2H), 4.12 (t, J=5.13 Hz, 2H), 3.88-3.79 (m, 5H), 3.13-2.93 (m, 3H), 2.72-2.65 (m, 1H), 2.27-2.05 (m, 2H); $^{13}$C NMR (75 MHz) δ 155.55, 149.74, 148.30, 141.11, 138.89, 126.85, 125.00, 123.04, 122.79, 121.78, 121.09, 119.68, 114.19, 112.71, 111.97, 110.15, 103.65, 101.27, 69.34, 68.80, 67.04, 55.92, 52.00, 48.67, 28.59; mass spectrum, m/z 420 ($M^+$). Exact mass calcd for $C_{25}H_{28}N_2O_4$: 420.20491. Found 420.20878.

G. REFERENCES

The following references, to the extent that they provide exemplary procedural or other details supplementary to those set forth herein, are specifically incorporated herein by reference.

Albers and Augood, *Trends Neurosci.*, 24:347-353 (2001).
Baartscheer et al., *Cardiovasc Res.* 58:99-108 (2003).
Barry et al., *Circulation*, 107:2395-2397 (2003).
Berr, *J Nutr. Health Aging*, 6:261-266 (2002).
Bers, *Nature*, 415:198-205 (2002).
Bezprozvanny, et al., *Nature*, 351:751-754 (1991).
Bristow et al., *Circulation*, 94:2807-2816 (1996).
Bundgaard, Design of Prodrugs, pp. 7-9, 21-24, Elsevier, Amsterdam 1985.
Butler et al., *Biophys Chem.*, 119:307-315 (2006).
Farrell et al., *JAMA*, 287:890-897 (2002).
Fill and Copello, *Physiol Rev.*, 82:893-922 (2002).
Foody et al., *Scientific Review, JAMA*, 287:883-889 (2002).
Gheorghiade and Eichhorn, *Am J. Med.*, 110 Suppl 7A:68S-73S (2001).
Hjalmarson, *Basic Res Cardiol.*, 95 Suppl 1:141-5 (2000).
Honen et al., *J Membr Biol.*, 196:95-103 (2003).
Jiang et al., *PNAS*, 101: 13062-13067 (2004).
Jenner, *Ann. Neurol.*, 53:S260S38 (2003).
Ko et al., *Arch Intern Med.*, 164:1389-1394 (2004).
Kutscher and Reichert, Pharmaceutical Substances—Syntheses, Patents, Applications, Thieme, Stuttgart, 2001, 4$^{th}$ ed., pp 364-365 and references cited therein.
Lakatta, *Cardiovasc Res.*, 26:193-214 (1992).
Lavie, *Sleep Med. Rev.*, 7:35-51 (2003).
Liang, et al., *Bioorganic & Medicinal Chemistry*, 10:719-730 (2002).
Marks et al., *J Cell Physiol.*, 190:1-6 (2002).
Miller L., *Rev Cardiovasc Med.*, 4 Suppl 2:S21-9 (2003).
Mohanakumar et al., *Ann. N.Y. Acad. Sci.*, 962:389-401 (2002).
Nakai et al., *FEBS Lett.*, 271:169-177 (1990).
Okafor et al., *BMC Physiol.*, 3:6 (2003).
Otsu et al., *J Biol. Chem.*, 265:13472-13483 (1990).
Pogwizd and Bers, *Trends in Cardiovascular Medicine*, 14:61-66 (2004).
Pong, *Expert. Opin. Biol. Ther.*, 3:127-139 (2003).
Priori et al., *Circulation*, 103:196-200 (2001).
Puccio and Koenig, *Curr. Opin. Genet. Dev.*, 12:272-277 (2002).
Rando, *Am. J. Phys. Med. Rehabil.*, 81:S175-S186 (2002).
Sanguinetti and Bennett, *Circ Res.*, 93:491-499 (2003).
Schwarz et al., *J Cardiovasc Pharmacol Ther.*, 8:207-215 (2003).
Srikrishna and Viswajanani, *Tetrahedron*, 51:3339-3344 (1995).
Thorpe et al., *Health Aff.*, 2004:hlthaff.w4.437.
Turchan et al., *Neurology*, 60:307-314 (2003).
Vermeulen et al., *Cardiovasc Res.*, 28:1547-1554 (1994).
Wiedemann, et al. Ger. Offen. 1979, DE 2815926 19791018.
Xiao et al., *Circ Res.*, 96:847-855 (2005).
Yao et al., *Circ J.*, 67:83-90 (2003).
Zhao et al., *J Biol. Chem.*, 274:25971-25974 (1999).
Zucchi and Ronca-Testoni, *Pharmacol Rev.*, 49:1-51 (1997).

As will be apparent to those skilled in the art, various modifications, adaptations and variations of the foregoing specific disclosure can be made without departing from the scope of the invention claimed herein. The various features and elements of the described invention may be combined in a manner different from the combinations described or claimed herein, without departing from the scope of the invention.

What is claimed is:

1. A compound of formula (I):

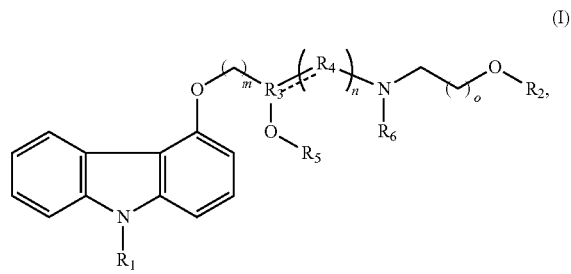

wherein:
R$_1$ is selected from the group consisting of H, lower alkyl, upper alkyl, lower alkylsulfonate, upper alkylsulfonate, —C(O)-lower alkyl, —C(O)-upper alkyl and acyl;
R$_2$ is selected from the group consisting of cycloalkyl, —OSO$_3^-$, a sugar, and phenyl optionally mono-, di- or tri-substituted with a group selected from halogen, lower alkyl and lower alkoxy;

R$_3$ is —CH—;
R$_4$ is —CH$_2$—;
R$_3$ and R$_4$ are joined by a single or double bond;
R$_5$ and R$_6$ are each independently selected from the group consisting of H, lower alkyl and acyl, or
R$_5$ and R$_6$ together form —C(O)—, —(CH$_2$)$_p$—, —(CH$_2$)$_q$C(O)— or —C(O)(CH$_2$)$_r$—, wherein p=1-7 and q and r are independently 1-6; and
n and o are each independently 1-5;
m is 2, 3, 4 or 5;
provided that when R$_1$ is H and R$_3$ and R$_4$ are single bonded, the following provisos apply:
when R$_5$ and R$_6$ are each —C(O)CH$_3$, then R$_2$ is not 2-methoxyphenyl;
when R$_5$ is —C(O)-t-butyl and R$_6$ is H, then R$_2$ is not 2-methoxyphenyl;
when R$_5$ and R$_6$ together form —C(O)—, then R$_2$ is not 2-methoxyphenyl; and
when R$_5$ is H or C$_1$-C$_6$ acyl, R$_6$ is H or C$_1$-C$_6$ alkyl, then R$_2$ is not phenyl that is mono- or di-substituted with any combination of halogen, C$_1$-C$_6$ alkyl, or C$_1$-C$_6$ alkoxy;
and provided that when R$_1$ is H, R$_3$ and R$_4$ are single bonded, and R$_5$ is H, the following provisos apply:
when R$_6$ is —C(O)CH$_3$, then R$_2$ is not 2-methoxyphenyl;
when R$_6$ is methyl or n-butyl, then R$_2$ is not 2-methoxyphenyl; and
when R$_6$ is H, then R$_2$ is not phenyl, 2-methylphenyl, 3-methylphenyl, 2,3-dimethylphenyl, 4-t-butylphenyl, 2-methoxyphenyl, 3-methoxyphenyl, 4-methoxyphenyl, 2-ethoxyphenyl, 2-chlorophenyl, 4-fluorophenyl, 5-fluoro-2-methoxyphenyl, or 2,6-dimethoxyphenyl.

2. The compound of claim 1, wherein R$_1$ is hydrogen.
3. The compound of claim 1, wherein R$_1$ is methyl.
4. The compound of claim 1, wherein R$_2$ is phenyl optionally mono-, di- or tri-substituted with a group selected from halogen, lower alkyl and lower alkoxy.
5. The compound of claim 4, wherein the phenyl group is tri-substituted at the 2, 4 and 5 positions.
6. The compound of claim 5, wherein the substituents at the 2, 4 and 5 positions are selected from the group consisting of methyl, methoxy and fluoro.
7. The compound of claim 1, wherein R$_2$ is 2-methoxyphenyl.
8. The compound of claim 1, wherein R$_2$ is a sugar.
9. The compound of claim 8, wherein the sugar is selected from the group consisting of ribosyl, 2'-deoxyribosyl and 2',3'-dideoxyribosyl.
10. The compound of claim 1, wherein at least one of R$_5$ and R$_6$ is hydrogen.
11. The compound of claim 10, wherein both R$_5$ and R$_6$ are hydrogen.
12. The compound of claim 1, wherein R$_5$ and R$_6$ together form —C(O)—, —(CH$_2$)$_p$—, —(CH$_2$)$_q$C(O)— or —C(O)(CH$_2$)$_r$—, wherein p=1-7 and q and r are independently 1-6.
13. The compound of claim 1, wherein at least one of n and o is 2, 3, 4 or 5.
14. The compound of claim 1, wherein m=2.
15. A pharmaceutical composition comprising the compound of claim 1.
16. The pharmaceutical composition of claim 15, wherein R$_1$ is hydrogen.
17. The pharmaceutical composition of claim 16, wherein R$_2$ is phenyl optionally mono-, di- or tri-substituted with a group selected from halogen, lower alkyl and lower alkoxy.
18. A method of treating a subject suffering from heart failure or arrhythmia associated with RyR2, comprising the step of administering to the subject the compound of claim 1.
19. The method of claim 18, wherein store-overload-induced Ca$^{2+}$ release is inhibited.
20. The method of claim 18, wherein Ca$^{2+}$-induced Ca$^{2+}$ release is minimally inhibited or not inhibited.

* * * * *